(12) United States Patent
Tanaka et al.

(10) Patent No.: US 8,211,009 B2
(45) Date of Patent: Jul. 3, 2012

(54) ENDOSCOPE BENDING CONTROL APPARATUS AND ENDOSCOPE SYSTEM

(75) Inventors: Hideki Tanaka, Tama (JP); Jun Hasegawa, Hino (JP); Toshio Nakamura, Hachioji (JP)

(73) Assignee: Olympus Medical Systems Corp., Tokyo (JP)

(*) Notice: Subject to any disclaimer, the term of this patent is extended or adjusted under 35 U.S.C. 154(b) by 219 days.

(21) Appl. No.: 12/764,482

(22) Filed: Apr. 21, 2010

(65) Prior Publication Data

US 2010/0204547 A1    Aug. 12, 2010

Related U.S. Application Data

(63) Continuation of application No. PCT/JP2008/068790, filed on Oct. 16, 2008.

(30) Foreign Application Priority Data

Nov. 29, 2007 (JP) .................................. 2007-309233
Dec. 7, 2007 (JP) .................................. 2007-317369
Dec. 26, 2007 (JP) .................................. 2007-334898

(51) Int. Cl.
*A61B 1/04* (2006.01)
(52) U.S. Cl. ......... 600/117; 600/118; 600/146; 600/109
(58) Field of Classification Search .................. 600/117, 600/118, 146, 103, 109
See application file for complete search history.

(56) References Cited

U.S. PATENT DOCUMENTS

| 4,910,590 | A | * | 3/1990 | Gillies et al. | 348/65 |
|---|---|---|---|---|---|
| 4,916,533 | A | * | 4/1990 | Gillies et al. | 348/65 |
| 4,982,725 | A | * | 1/1991 | Hibino et al. | 600/117 |
| 5,018,509 | A | * | 5/1991 | Suzuki et al. | 600/115 |
| 5,036,464 | A | * | 7/1991 | Gillies et al. | 600/145 |
| 5,347,987 | A | * | 9/1994 | Feldstein et al. | 600/109 |
| 5,469,254 | A | * | 11/1995 | Konomura | 356/241.1 |
| 5,658,238 | A | | 8/1997 | Suzuki et al. | |

(Continued)

FOREIGN PATENT DOCUMENTS

EP    1 437 083 A1    7/2004

(Continued)

OTHER PUBLICATIONS

Supplementary European Search Report dated Nov. 23, 2011 from corresponding European Patent Application No. EP 08 85 3729.5.

(Continued)

*Primary Examiner* — John P Leubecker
(74) *Attorney, Agent, or Firm* — Scully, Scott, Murphy & Presser, P.C.

(57) ABSTRACT

An endoscope bending control apparatus includes: an image feature value calculating section for calculating, based on an endoscopic image, an image feature value related to a luminal dark part; a bending control section for performing bending control on a bending portion in either one of a first bending operation mode in which a position of the luminal dark part is set as an insertion target and a distal end of the insertion portion is directed to the position and a second bending operation mode in which the distal end of the insertion portion is directed in a direction of the position of the luminal dark part; an operation mode switching section for switching an operation mode from one bending operation mode to the other according to a first switching condition based on the calculated image feature value; and a switching condition changing section for changing the first switching condition.

20 Claims, 25 Drawing Sheets

U.S. PATENT DOCUMENTS

| | | | |
|---|---|---|---|
| 7,258,664 B2 * | 8/2007 | Nishimura et al. | 600/117 |
| 7,811,226 B2 * | 10/2010 | Nishimura et al. | 600/117 |
| 7,854,699 B2 * | 12/2010 | Nishimura et al. | 600/117 |
| 7,878,971 B2 * | 2/2011 | Nishimura et al. | 600/117 |
| 7,905,829 B2 * | 3/2011 | Nishimura et al. | 600/117 |
| 8,038,605 B2 * | 10/2011 | Tsuji et al. | 600/152 |
| 2005/0010082 A1 | 1/2005 | Nishimura et al. | |
| 2007/0161857 A1 | 7/2007 | Durant et al. | |
| 2007/0173690 A1 | 7/2007 | Nishimura et al. | |
| 2007/0179338 A1 | 8/2007 | Nishimura et al. | |
| 2007/0191679 A1 | 8/2007 | Nishimura et al. | |
| 2007/0191681 A1 | 8/2007 | Nishimura et al. | |
| 2008/0097150 A1 * | 4/2008 | Hasegawa et al. | 600/109 |

FOREIGN PATENT DOCUMENTS

| | | |
|---|---|---|
| EP | 1 800 593 A1 | 6/2007 |
| JP | 5-228102 | 9/1993 |
| JP | 7-155289 | 6/1995 |
| JP | 2002-248073 | 9/2002 |
| JP | 2003-093328 | 4/2003 |
| JP | 2004-329761 | 11/2004 |
| JP | 2005-518855 | 6/2005 |
| JP | 2006-042902 | 2/2006 |
| JP | 2006-055349 | 3/2006 |
| JP | 2006-116289 | 5/2006 |
| JP | 2007-282857 | 11/2007 |
| WO | WO 03/026497 A1 | 4/2003 |
| WO | WO 2004/029782 A2 | 4/2004 |
| WO | WO 2007/119296 A1 | 10/2007 |

OTHER PUBLICATIONS

International Publication No. WO 03/073921 A1, dated Sep. 12, 2003 (abstract only).

International Search Report dated Jan. 20, 2009.

* cited by examiner

INSERTION SHAPE DATA

FRAME DATA

COIL COORDINATES

| | PATH VALUE P1 (RECTUM) | PATH VALUE P2 (SIGMOID COLON) | PATH VALUE P3 (DESCENDING COLON) | MAGNITUDE RELATION |
|---|---|---|---|---|
| LUMINAL DARK PART DISTANCE D | D1 | D2 | D3 | D3>D1=D2 |
| HALATION PIXEL RATIO a | a1 | a2 | a3 | a2=a3<a1 |
| DARK-PART PIXEL RATIO b | b1 | b2 | b3 | b1=b3<b2 |
| INSERTION LENGTH L | L1 | L2 | L3 | L1<L2<L3 |
| (LUMINAL DARK PART) ELLIPTIC MAJOR AXIS/ MINOR AXIS RATIO r | r1 | | | r1<1.4 |
| EDGE LINE MAXIMUM LENGTH e | | e2 | | e2<IMAGE WIDTH×0.8 |

FIG.15

PATH LIST = PATH VALUE P1
CENTERING MODE: D > D1, a < a1, b < b1
SEARCHING MODE: D ≤ D1, a ≥ a1, b ≥ b1
TRANSITION (SWITCHING) CONDITION TO NEXT PATH VALUE P2
    L > L1, r < r1

PATH LIST = PATH VALUE P2
CENTERING MODE: D > D2, a < a2, b < b2
SEARCHING MODE: D ≤ D2, a ≥ a2, b ≥ b2
TRANSITION (SWITCHING) CONDITION TO NEXT PATH VALUE P3
    L > L2, e > e2

PATH LIST = PATH VALUE P3
CENTERING MODE: D > D3, a < a3, b < b3
SEARCHING MODE: D ≤ D3, a > a3, b ≥ b3
TRANSITION (SWITCHING) CONDITION TO NEXT PATH VALUE
    L > L3, EDGE CORNER IS PRESENT

FIG.16A

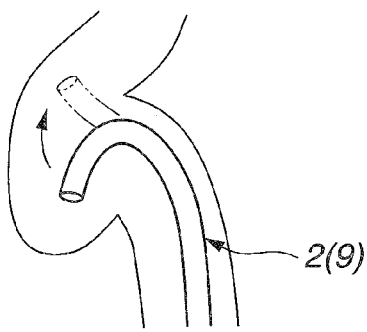

DARK PART REGION

DARK PART REGION

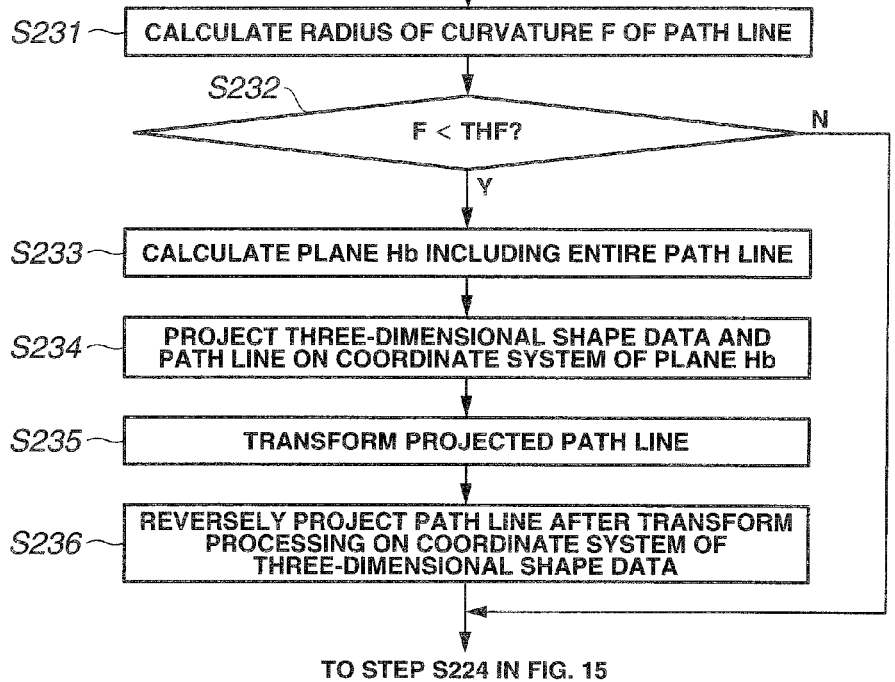
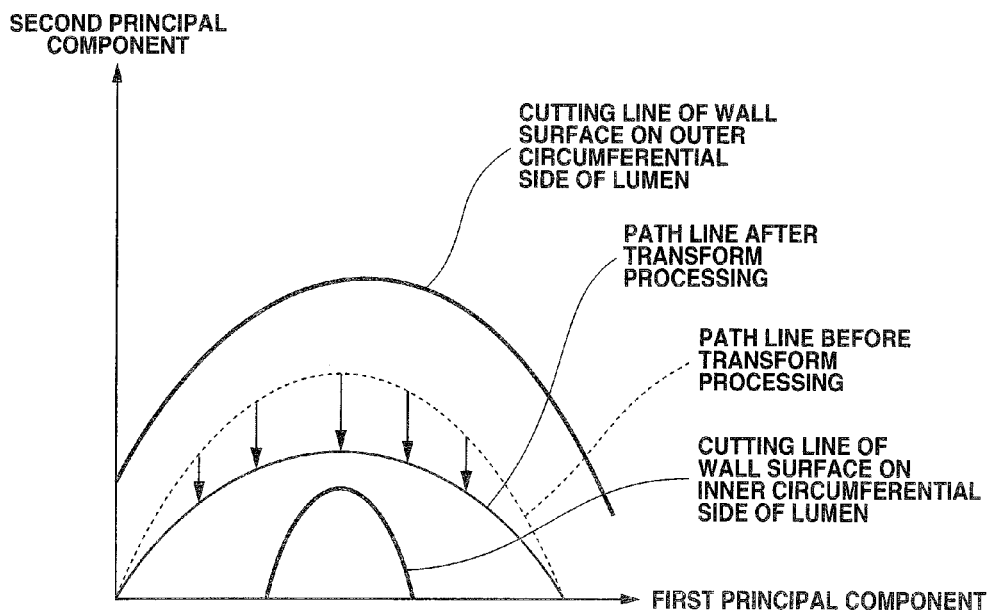

ENDOSCOPE BENDING CONTROL APPARATUS AND ENDOSCOPE SYSTEM

CROSS REFERENCE TO RELATED APPLICATION

This application is a continuation application of PCT/JP2008/068790 filed on Oct. 16, 2008 and claims the benefit of Japanese Patent Applications No. 2007-309233 filed in Japan on Nov. 29, 2007, No. 2007-317369 filed in Japan on Dec. 7, 2007, and No. 2007-334898 filed in Japan on Dec. 26, 2007, the entire contents of each of which are incorporated herein by their reference.

BACKGROUND OF THE INVENTION

1. Field of the Invention

The present invention relates to an endoscope bending control apparatus and an endoscope system for performing endoscopic examination by inserting an endoscope into a body cavity and the like.

2. Description of the Related Art

In recent years, endoscopes have been widely used to examine and diagnose inside of a body cavity or a lumen. When endoscopes are used, it is desirable that an insertion portion is smoothly inserted into a body cavity.

For example, Japanese Patent Application Laid-Open Publication No. 2003-93328 as a first prior art example discloses to detect a direction in which a distal end portion of an insertion portion is to be inserted, that is, a target position, based on an endoscopic image and set the direction of the target position as an insertion direction.

In addition, Japanese Patent Application Laid-Open Publication No. 2006-116289 as a second prior art example discloses a bending control apparatus for performing bending control at the time of insertion of an endoscope by selecting a first bending control method based on an image picked up by an endoscope and a second bending control method based on a detected image of an endoscope insertion shape and a CT image.

SUMMARY OF THE INVENTION

An endoscope bending control apparatus according to one aspect of the present invention comprises: an image feature value calculating section for calculating, based on an endoscopic image acquired by an image pickup device in an endoscope including the image pickup device and a bending portion on a distal end side of an insertion portion, an image feature value related to a luminal dark part in a lumen into which the insertion portion is inserted; a bending control section for performing bending control on the bending portion in either one of a first bending operation mode in which a position of the luminal dark part is set as an insertion target based on the calculated image feature value and a distal end of the insertion portion is directed to the position and a second bending operation mode in which a current position of the luminal dark part is estimated with reference to history information including the position of the luminal dark part calculated in the past and the distal end of the insertion portion is directed in a direction of the estimated position of the luminal dark part; an operation mode switching section for switching an operation mode from one of the first and the second bending operation modes to the other of the first and the second bending operation modes according to a first switching condition based on the calculated image feature value; and a switching condition changing section for changing a switching condition from the first switching condition used for switching between the bending operation modes to a second switching condition different from the first switching condition.

An endoscope system according to one aspect of the present invention comprises: an endoscope including at a distal end side of an insertion portion thereof an image pickup device and a bending portion; a signal processing apparatus to which the endoscope is connected, the signal processing apparatus generating an endoscopic image based on an output signal from the image pickup device; an image feature value calculating section for calculating, based on the endoscopic image, an image feature value related to a luminal dark part in a lumen into which the insertion portion is inserted; a bending control section for performing bending control on the bending portion in either one of a first bending operation mode in which a position of the luminal dark part is set as an insertion target based on the calculated image feature value and a distal end of the insertion portion is directed to the position and a second bending operation mode in which a current position of the luminal dark part is estimated with reference to history information including the position of the luminal dark part calculated in the past and the distal end of the insertion portion is directed in a direction of the estimated position of the luminal dark part; an operation mode switching section for switching an operation mode from one of the first and the second bending operation modes to other of the first and the second bending operation modes according to a first switching condition based on the calculated image feature value; and a switching condition changing section for changing a switching condition from the first switching condition used for switching between the bending operation modes to a second switching condition different from the first switching condition.

BRIEF DESCRIPTION OF THE DRAWINGS

FIG. 15 is a view showing specific examples of contents of path values sequentially set based on path lists.

FIG. 16A is an illustration diagram illustrating a fold push-in mode.

FIG. 31 is a view showing an example of processing which can be added to the processing in the flowchart in FIG. 26.

FIG. 32 is a schematic diagram related to a brief overview of the processing in the flowchart in FIG. 31.

DETAILED DESCRIPTION OF THE PREFERRED EMBODIMENT(S)

Hereinafter, embodiments of the present invention will be described with reference to the drawings.

(First Embodiment)

Figure 1:
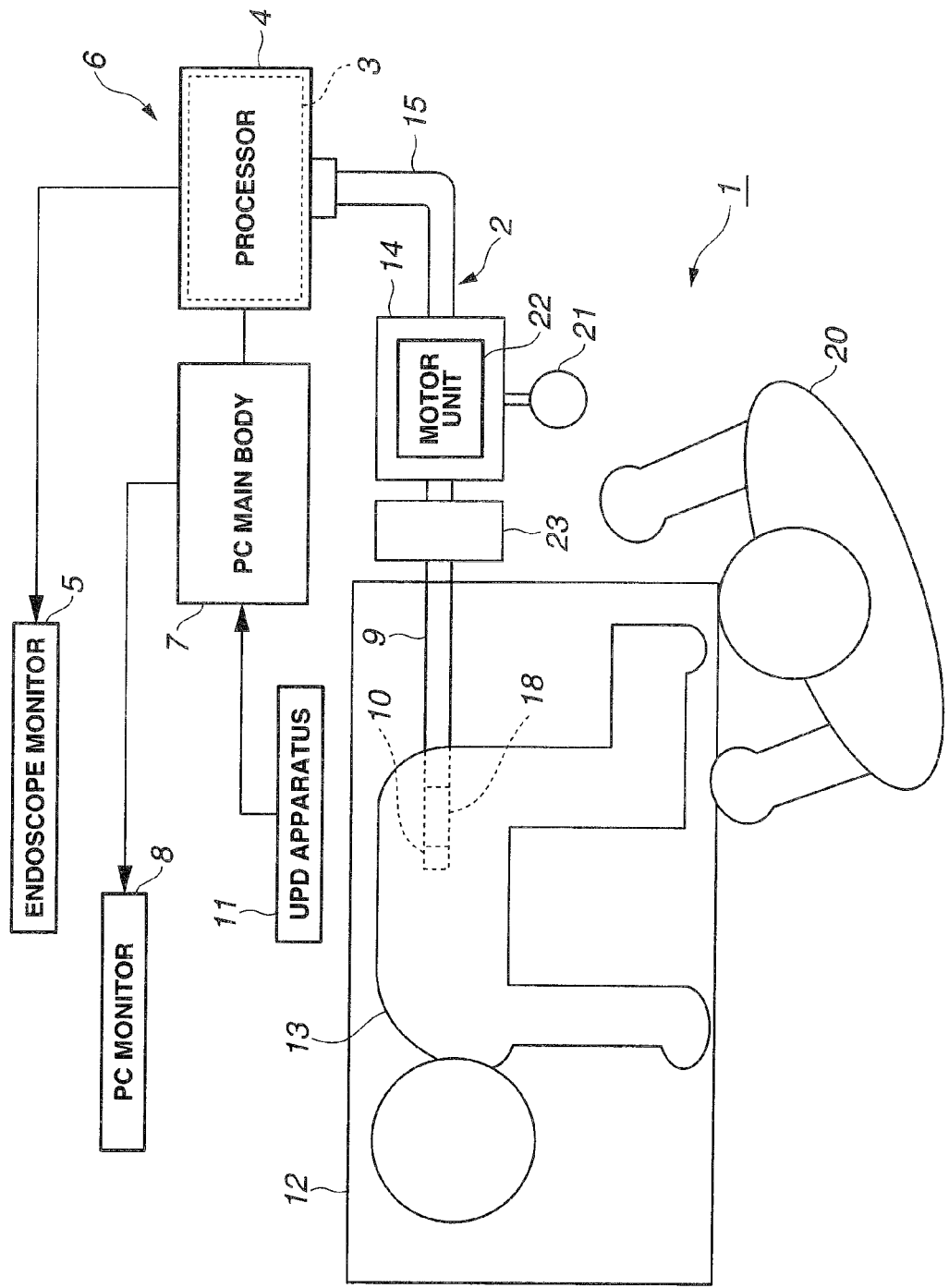
FIG. 1 is a configurational view showing a configuration of an endoscope system according to a first embodiment of the present invention in an example of use.
Figure 2:
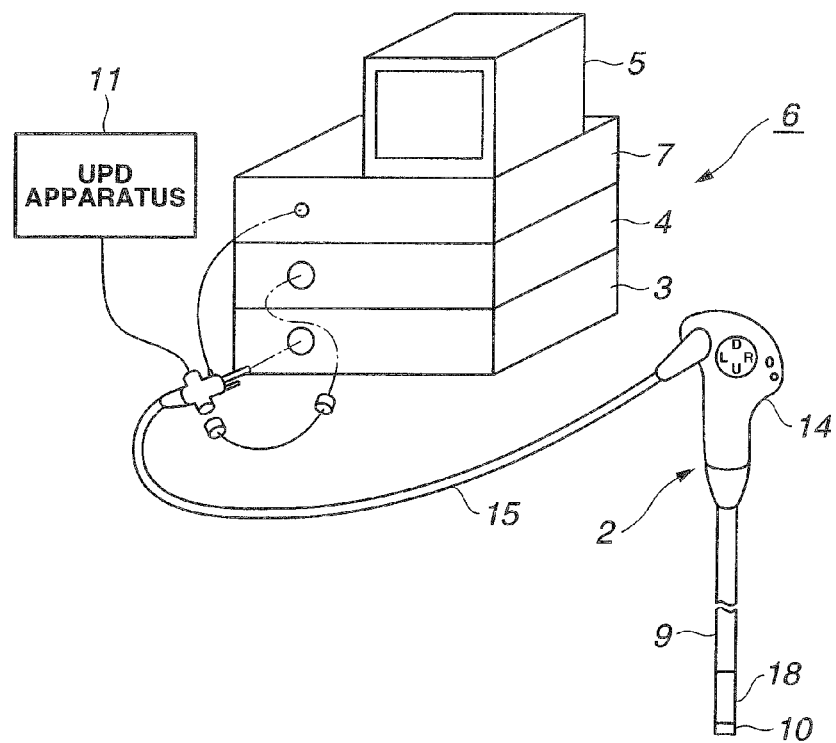
FIG. 2 is a view showing an example of an appearance of an endoscope apparatus.
Figure 3:
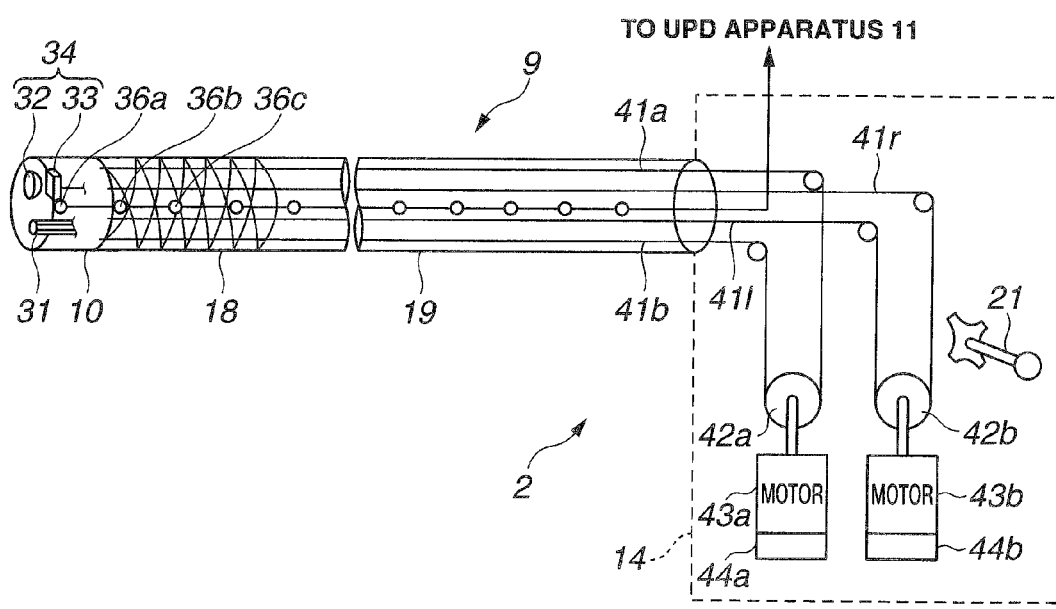
FIG. 3 is a view showing an internal configuration of an endoscope.
Figure 4:
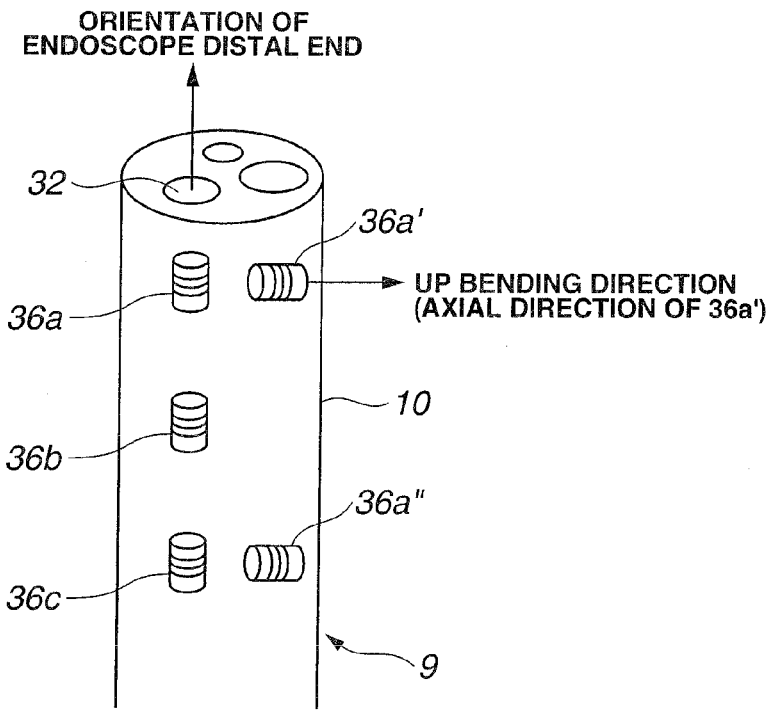
FIG. 4 is a view showing an arrangement example of coils located on a distal end side of an insertion portion.
Figure 5:
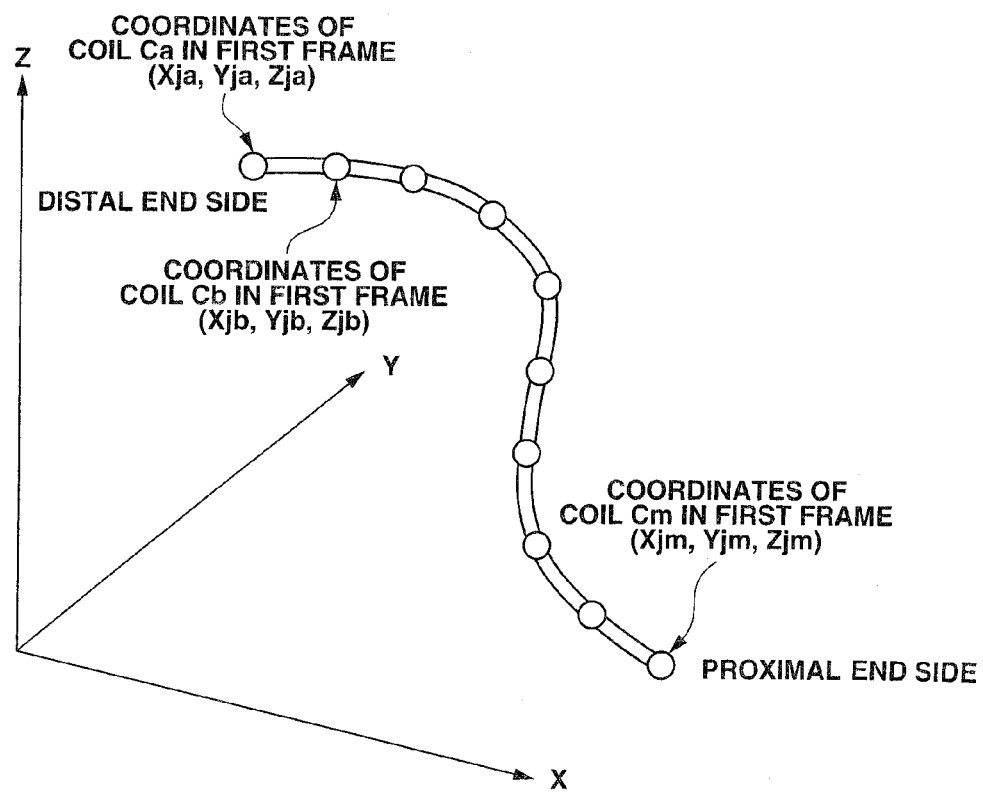
FIG. 5 is a view showing an insertion shape to be detected.

FIGS. 1 to 15 relate to the first embodiment of the present invention. FIG. 1 shows a configuration of an endoscope system according to the first embodiment of the present invention in an example of use. FIG. 2 shows an example of an appearance of an endoscope apparatus. FIG. 3 shows an internal configuration of an endoscope. FIG. 4 shows an arrangement example of coils located on a distal end side of an insertion portion. FIG. 5 shows an insertion shape to be detected.

Figure 6A:
FIG. 6A is a view showing an example of insertion shape data.
Figure 6B:
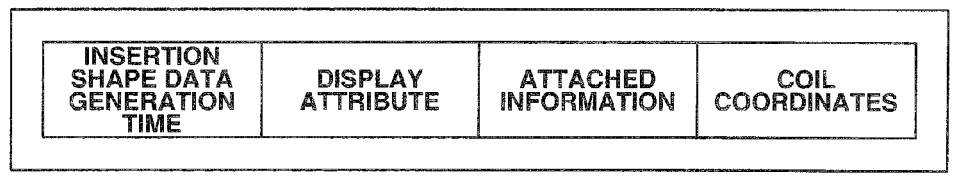
FIG. 6B is a view showing an example of frame data.
Figure 6C:
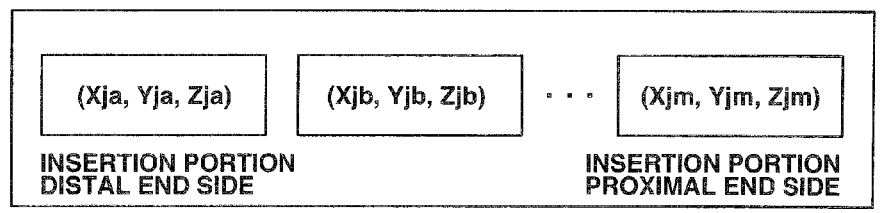
FIG. 6C is a view showing an example of coil coordinate data.
Figure 7:
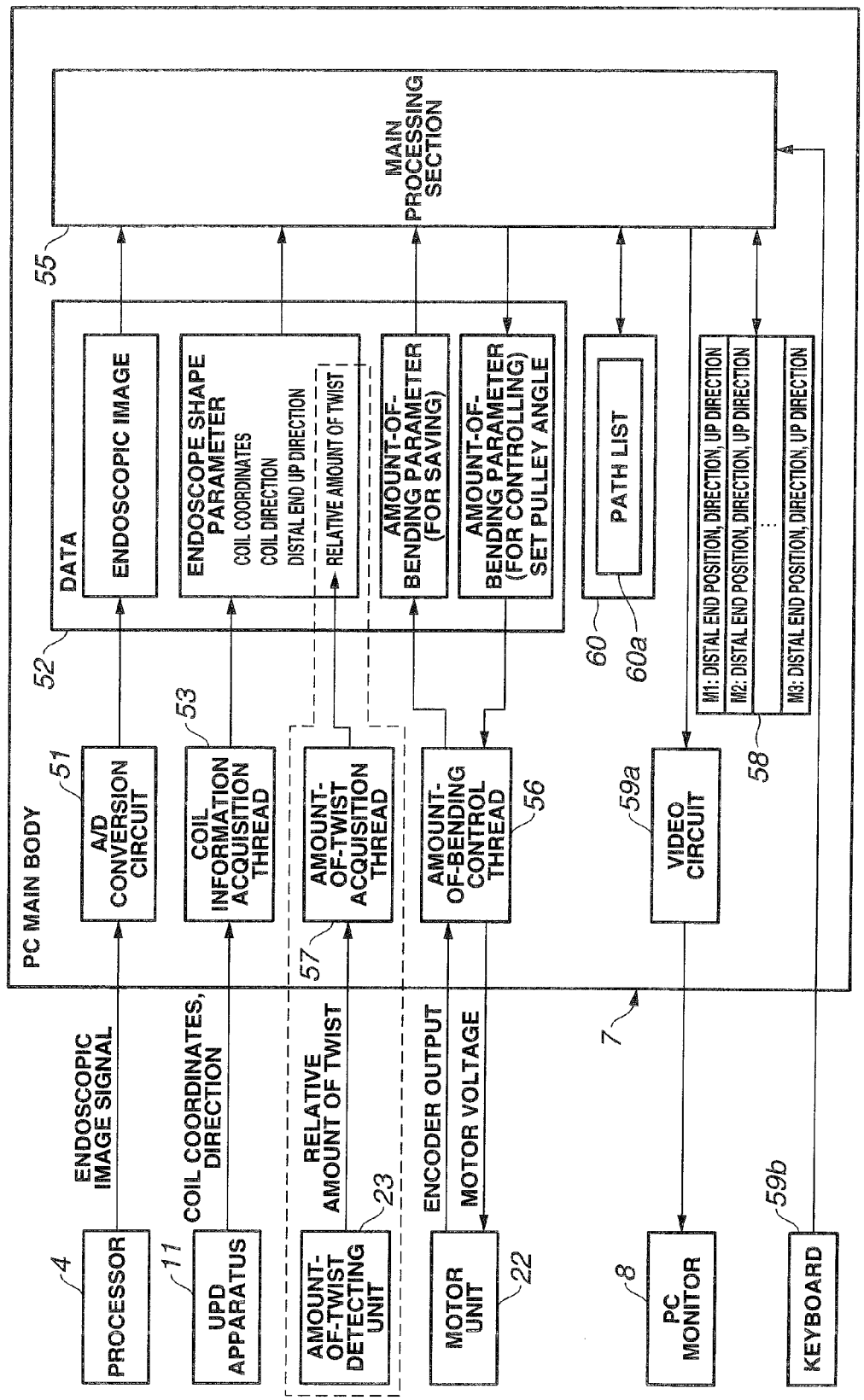
FIG. 7 is a diagram showing a functional block configuration of a PC main body.
Figure 8:
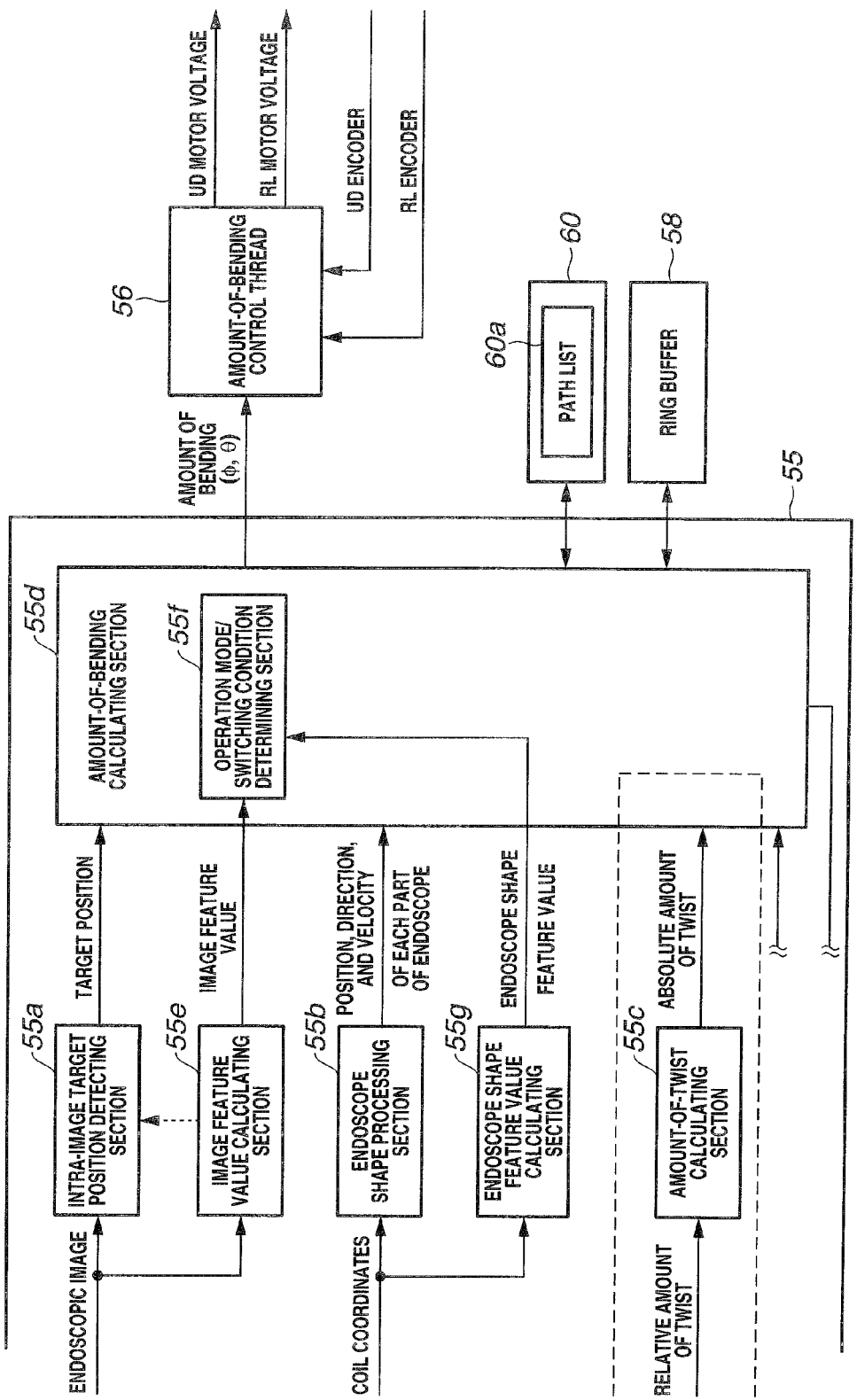
FIG. 8 is a diagram showing a functional block configuration of a main processing section.
Figure 9:
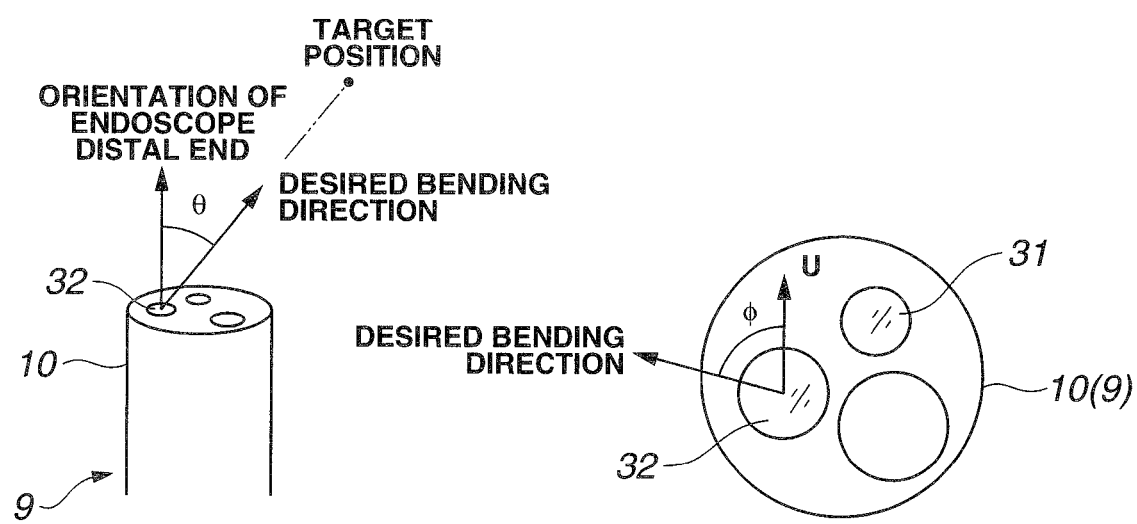
FIG. 9 is a view showing angles $\theta$ and $\phi$ which are bending angles formed between a direction of an endoscope distal end and a desired bending direction.
Figure 10:
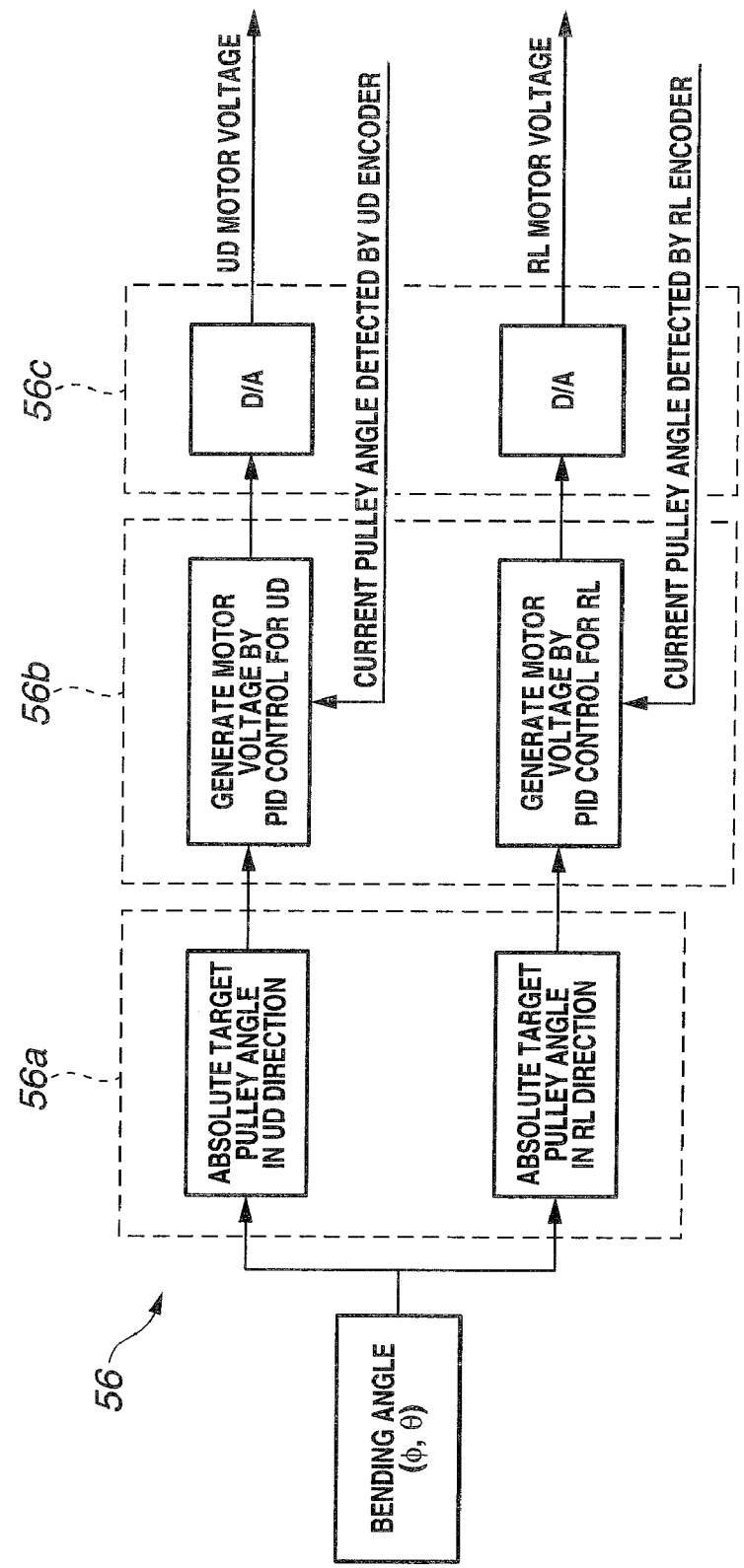
FIG. 10 is a block diagram showing a processing function for generating motor voltages based on the bending angles in FIG. 9.

FIGS. 6A to 6C show an example of insertion shape data, an example of frame data, and an example of coil coordinate data, respectively. FIG. 7 shows a functional block configuration of a PC main body. FIG. 8 shows a functional block configuration of a main processing section. FIG. 9 shows angles $\theta$ and $\phi$ which are bending angles formed between a direction of an endoscope distal end and a desired bending direction. FIG. 10 shows a processing function for generating motor voltages based on the bending angles in FIG. 9.

Figures 11, 12:
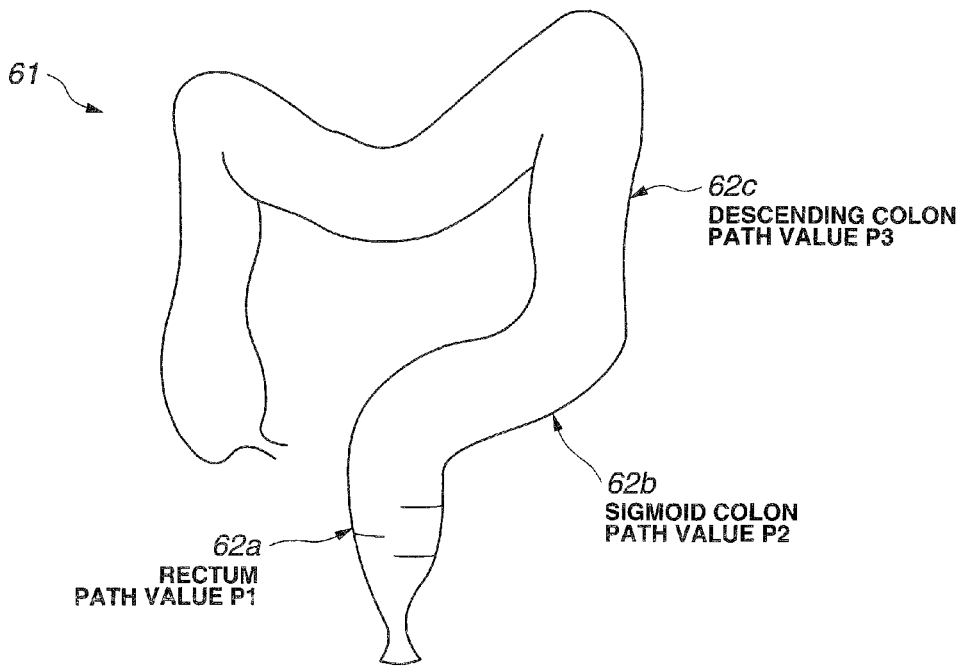
FIG. 11 is a view showing parameters and the like used for switching conditions for switching among operation modes and conditions for further switching the switching conditions.
FIG. 12 is a view illustrating a large intestine as an insertion target region.
Figure 13:
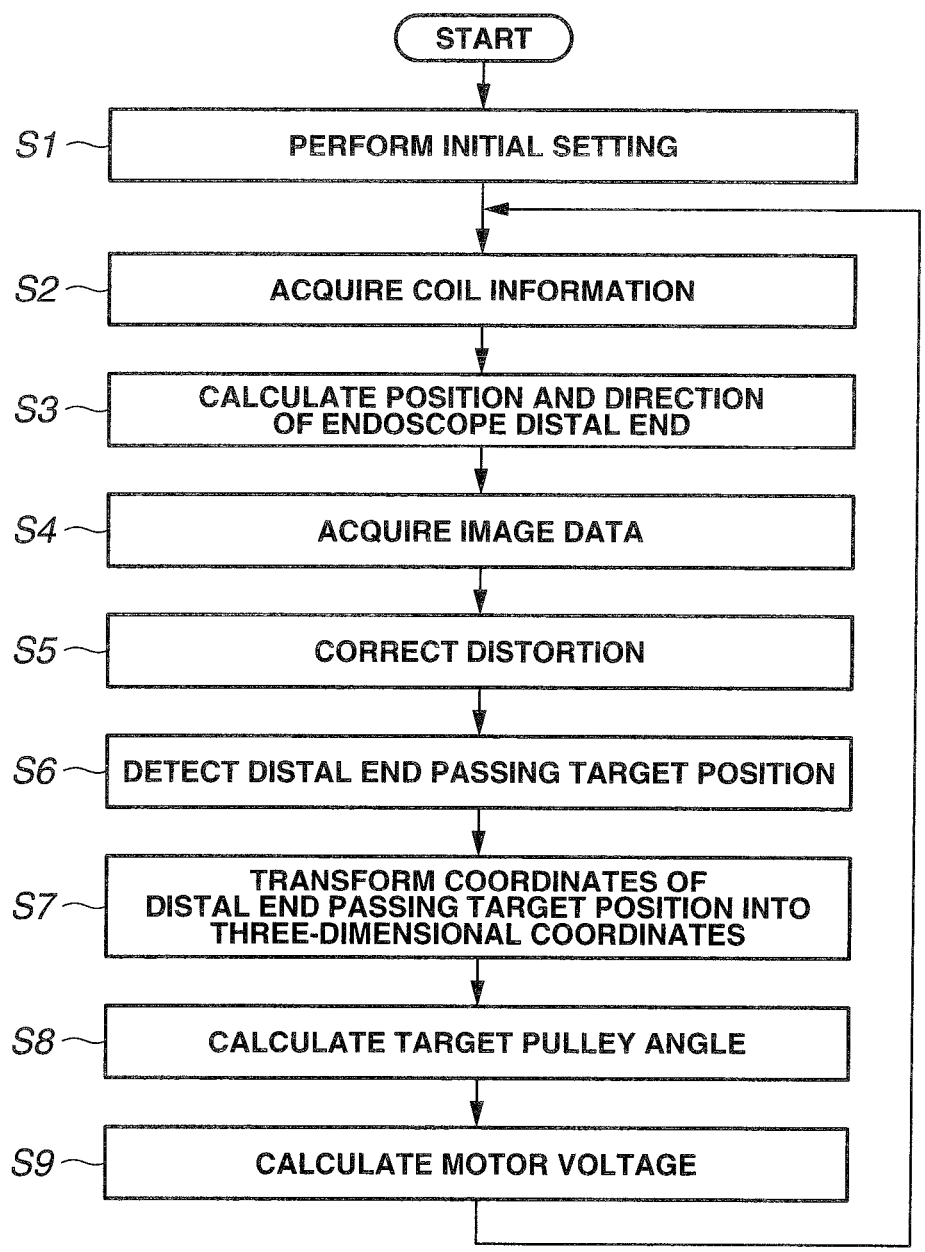
FIG. 13 is a flowchart showing an operation content of bending control.
Figure 14:
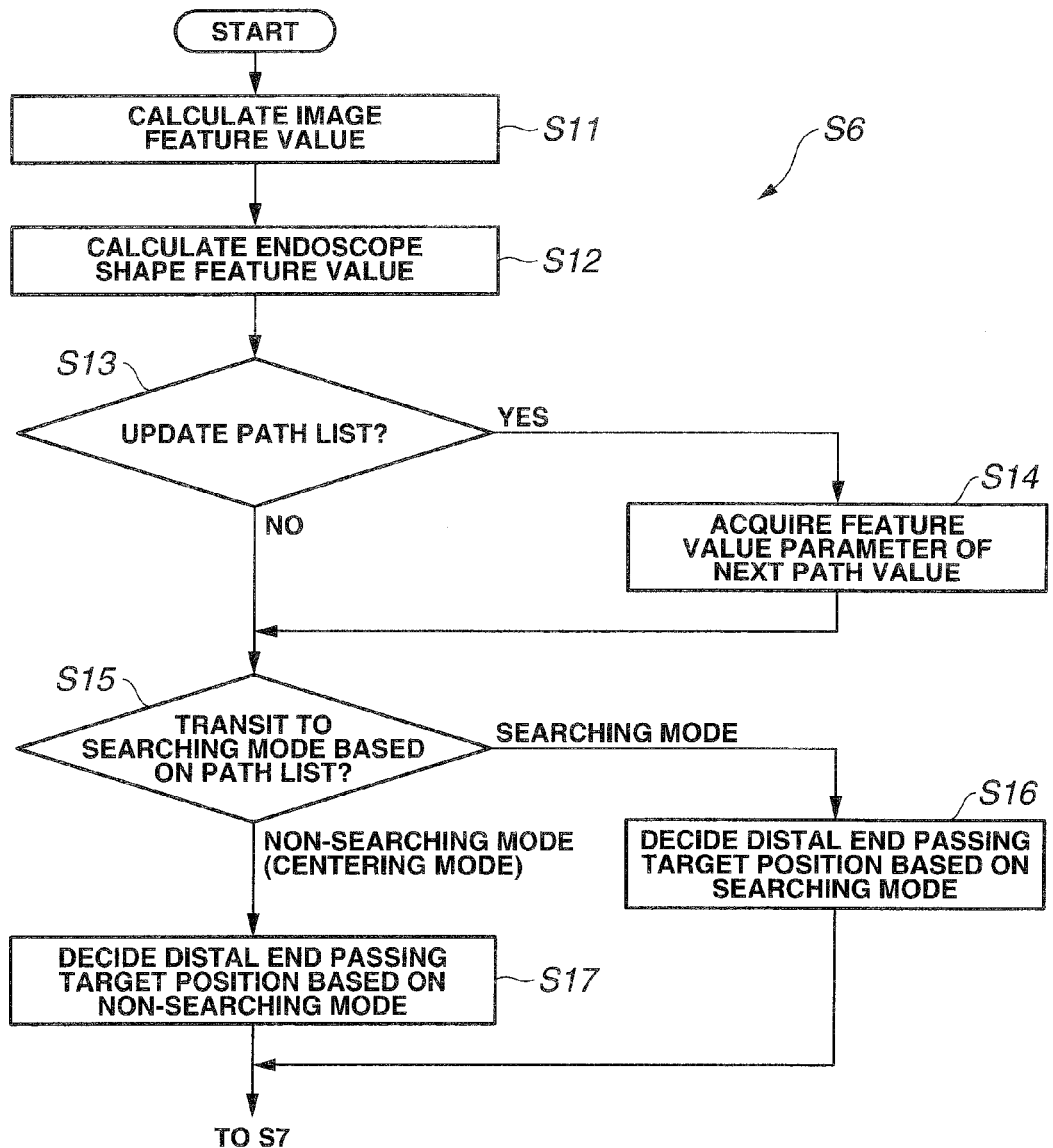
FIG. 14 is a flowchart showing an operation content of detection of a distal end passing target position in FIG. 13.

FIG. 11 shows parameters and the like used for switching conditions for switching among operation modes and conditions for further switching the switching conditions. FIG. 12 shows a large intestine as an insertion target region. FIG. 13 shows an operation content of bending control. FIG. 14 shows an operation content of detection of a distal end passing target position in FIG. 13. FIG. 15 shows specific example of the path list on which feature value parameters for specifying switching conditions and the like for path values as path sites along an insertion path are listed.

As shown in FIG. 1, an endoscope system 1 according to the first embodiment of the present invention includes: an endoscope 2 for performing endoscopic examination; a light source apparatus 3; an endoscope apparatus 6 including a processor 4 and an endoscope monitor 5; a personal computer main body (hereinafter referred to shortly as PC main body) 7 for performing image processing on an endoscopic image picked up by the endoscope 2 and performing bending control processing; a PC monitor 8; and an UPD (registered trademark in Japan and U.S.A. owned by Olympus corp. Hereinafter, only referred to as UPD) apparatus 11 as endoscope shape detecting means for performing insertion shape detection including a position detection for detecting at least distal end side of an insertion portion 9 of the endoscope 2.

As shown in FIG. 1, the endoscope 2 includes the elongated insertion portion 9 to be inserted in a body cavity (or a lumen) of a patient 13 as a subject lying on a bed 12, and an operation portion 14 provided on a rear end of the insertion portion 9. A connector located on an end portion of a universal cable 15 extended from the operation portion 14 is connected to the light source apparatus 3 for emitting illumination light and the processor 4 as a signal processing apparatus for performing signal processing.

As shown in FIG. 2, the insertion portion 9 includes a distal end portion 10 provided at a distal end thereof, a bendable bending portion 18 provided at a rear end of the distal end portion 10, a flexible portion 19 having flexibility and extended from a rear end of the bending portion 18 to the operation portion 14.

The operation portion 14 is provided with a joystick 21, for example, as bending instruction operation means that performs bending instruction operation to bend the bending portion 18 in a direction desired by an operator 20.

The operator 20 operates the joystick 21, thereby capable of electrically bending the bending portion 18 through a motor unit 22 configuring electric bending driving means provided in the operation portion 14.

In addition, when the operator 20 selects an automatic bending control mode to be described later, the bending control of the bending portion 18 is electrically performed through the motor unit 22 by the motor control by the PC main body 7 such that the distal end side of the insertion portion 9 is directed in a running direction of the lumen through which the insertion portion 9 is inserted.

Furthermore, as shown in FIG. 1, an amount-of-twist detecting unit 23 is provided, for example, on an outer circumferential surface on a rear end side of the insertion portion 9 so as to be able to detect the amount of twist when the insertion portion 9 is twisted around the axis thereof.

An endoscope bending control apparatus of present embodiment is mainly configured of the PC main body 7 for performing bending control of the motor unit 22 which electrically bends and drives the bending portion 18 of the endoscope 2.

Note that the endoscope apparatus 6 in FIG. 1 has an appearance as shown in FIG. 2, for example. In FIG. 2, the PC main body 7 configures the endoscope apparatus 6, as a bending control unit of the motor unit 22 in the endoscope 2.

In addition, the joystick 21 is used for the endoscope 2 in FIG. 1. However, the bending instruction operation means may be formed by a joypad as shown in FIG. 2.

The present embodiment includes, in addition to a normal bending control mode by manual bending in which the operator 20 operates, for example, the joystick 21 as the bending instruction operation means by hand (manually) to set the distal end portion 10 side in the running direction of the lumen and insert the endoscope 2, the automatic bending control mode in which the position of the luminal dark part is three-dimensionally estimated (as a target position) from an endoscopic image by image processing and the insertion shape of the distal end side of the insertion portion 9 is estimated, and the bending portion 18 is electrically bent and controlled such that the distal end of the insertion portion 9 is directed in the direction of the target position.

As shown in FIG. 3, a light guide 31 for transmitting illumination light is inserted through the insertion portion 9. The light guide 31 passes through the operation portion 14 and the universal cable 15 shown in FIG. 1 or FIG. 2, and the rear end of the light guide 31 is connected to the light source apparatus 3.

Illumination light from a lamp, not shown, in the light source apparatus 3 is incident on the rear end surface of the light guide 31. The illumination light transmitted by the light guide 31 is emitted forward from the distal end surface of the light guide which is fixed to an illumination window provided in the distal end portion 10.

The illumination light emitted forward of a longitudinal axis of the insertion portion 9 from the illumination window illuminates forward of the longitudinal axis in the body cavity through which the insertion portion 9 is inserted. As shown in FIG. 3, an objective lens 32 for forming an optical image is attached to an observation window provided adjacently to the illumination window, and an observation field of view or an image pickup range is illuminated with the illumination light.

An image pickup apparatus 34 is formed by the objective lens 32 for forming an optical image and a CCD 33, for example, as a solid-state image pickup device which is arranged at an image-forming position of the objective lens.

A CCD output signal or an image pickup signal photoelectrically converted by the CCD 33 is inputted to the processor 4. The processor 4 performs a signal processing on the image pickup signal, thereby generating an RGB signal and the like as an endoscopic image signal (video signal) for displaying an endoscopic image on the endoscope monitor 5. The endoscopic image signal is inputted to the endoscope monitor 5 and the endoscopic image is displayed in an endoscopic image display area on the endoscope monitor 5.

Note that the endoscopic image signal is inputted also to the PC main body 7 as an image processing/motor controlling apparatus for performing image processing and motor control (or bending control), and is used for the image processing for detecting position information to insert the distal end of the insertion portion 9 in the running direction of the body cavity.

Furthermore, in the endoscope 2 according to the present embodiment, in order to detect the insertion shape (also referred to as endoscope shape) of the insertion portion 9, a plurality of UPD coils (hereinafter, just referred to as coils) 36a, 36b, 36c, etc., as position information generating means, each of which generates position information, are arranged from the distal end portion 10 to an appropriate position of the flexible portion 19 at predetermined intervals, for example.

By detecting the position of each of the coils 36a, 36b, 36c, etc., the insertion shape of the insertion portion 9 can be calculated. By detecting, in particular, the positions of the plurality of coils on the distal end side of the insertion portion 9, for example, the positions of the coils 36a, 36b and 36c, not only the distal end position of the insertion portion 9, but also the longitudinal axis direction (orientation) of the insertion portion 9 can be detected.

Furthermore, in the present embodiment, as shown in FIG. 4, in addition to the coils 36a, 36b and 36c arranged in the longitudinal direction, a coil 36a' is arranged adjacently to the coil 36a in the distal end portion 10 such that the solenoid axis (axis of winding) of the coil 36a' is set, for example, in the direction which is perpendicular to the coil 36a arranged along the longitudinal axis and which is the upper bending direction (hereinafter referred to as up bending direction or just as up-direction) when the bending portion 18 is bent.

In this case, the coil 36a and the coil 36a' are arranged such that the winding directions are perpendicular to each other. Note that the arrangement of the coils 36a and 36a' is not limited to the arrangement in which the winding directions of the coils are perpendicular to each other. The winding directions may be parallel to each other.

Note that, in FIG. 4, the coils 36c and 36a'' are arranged such that the arrangement relationship between the coil 36a'' and the coil 36c is the same as that between the above-described coils.

According to such an arrangement, by detecting the positions of the coils 36a, 36b, 36c, 36a', 36a'', etc., it is possible to detect not only the position of the distal end portion 10 but also the rotation angle around the (longitudinal) axis of the distal end portion 10 or the orientation (the up-direction and the upper direction of the CCD 33), in other words, the change in the rotation angle or the orientation due to the twist of the insertion portion 9. That is, these coils form a rotation angle detecting section.

The rear end side cables of the coils 36a, 36b, 36c, etc., are connected to the UPD apparatus 11.

In addition, the UPD apparatus 11 shown in FIG. 1 includes a UPD drive circuit, not shown, for causing the coils 36a, 36b, 36c, etc., to generate magnetic fields by applying a drive signal having a predetermined frequency, and a magnetic field detecting sense coil unit composed of a plurality of sense coils arranged in a predetermined positional relationship for detecting magnetic fields.

Furthermore, the UPD apparatus 11 incorporates a position detecting section that detects (calculates) the positions of the coils 36a, 36b, 36c, etc., based on detection signals from the plurality of sense coils, and an insertion shape calculating/displaying processing circuit that performs calculation processing of the insertion shape of the insertion portion 9 (endoscope 2) based on the position information of the coils 36a, 36b, 36c, etc., and a display processing of the calculated insertion shape, and includes a shape display monitor, not shown, that displays the insertion shape.

Note that at least the sense coil unit in the UPD apparatus 11 is arranged in the vicinity of the bed 12 in FIG. 1, and the sense coil unit detects the positions of the coils 36a, 36b, 36c, etc., in the coordinate system (referred to as the world coordinate system) which covers the three-dimensional region of the patient 13 lying on the bed 12, where the insertion portion 9 is inserted. In other words, the sense coil unit detects the three-dimensional coordinate positions of the coils in the world coordinate system.

Note that the amount-of-twist detecting unit 23 shown in FIG. 1, which detects the amount of twist of the insertion portion 9, is not an indispensable component when the coil 36a' as shown in FIG. 4 is provided to allow the orientation (up-direction) of the distal end portion 10 to be detected.

FIG. 5 shows an example of the insertion shape generated by the UPD apparatus 11. As shown in FIG. 5, the positions (Xji, Yji, Zji) (here, i=a, b . . . , m) of the coils 36a, 36b, 36c, etc., in a j-frame (j=0, 1, 2, etc.), for example, are calculated in the three-dimensional coordinate system, and by connecting the calculated positions, the insertion shape is generated.

The insertion shape data including the positions of the coils 36a, 36b, 36, etc., detected by the UPD apparatus 11 is configured as pieces of frame data related to the frames (that is, 0-th frame data, first frame data, etc.) as shown in FIG. 6A, and sequentially transmitted to the PC main body 7.

As shown in FIG. 6B, each piece of frame data as insertion state information includes data such as an insertion shape data generation time, a display attribute, attached information and three-dimensional coordinate data of the coils (coil coordinate data).

In addition, as shown in FIG. 6C, the coil coordinate data shows the three-dimensional coordinates of the coils 36a, 36b, 36c, etc., which are sequentially arranged from the distal end side to the proximal end side (operation portion 14 side) of the insertion portion 9.

On the other hand, the endoscopic image acquired by the image pickup apparatus 34 provided in the distal end portion 10 changes in accordance with the insertion amount of the insertion portion 9 into a body cavity (lumen such as a large intestine, in the following description).

Therefore, the position information of a luminal dark part in the lumen detected from the endoscopic image is transformed into that in the world coordinate system. Note that the position information of the luminal dark part corresponds to the running direction of the lumen, so that the position information is a target position for the distal end of the insertion portion which is to be inserted (introduced) to the deeper part of the lumen or a target position in the bending direction in which the distal end of the insertion portion is to be bent.

The observation direction (image pickup direction) of the image pickup apparatus 34 provided in the distal end portion 10 is parallel to the longitudinal axis of the insertion portion 9, in the endoscope 2. The above-described insertion direction or the bending direction is the same direction as the observation direction of the image pickup apparatus 34.

The information on the coil coordinate positions and the directions of the coils 36a, 36b, 36c, 36d, etc., detected by the coil position detecting section in the UPD apparatus 11 is also inputted to the PC main body 7 (see FIG. 7 to be described later).

As schematically shown in FIG. 3, the bending portion 18 is configured of a plurality of bending pieces rotatably connected to one another in the longitudinal direction. In addition, bending wires 41u, 41d, 41l and 41r are inserted through the insertion portion 9 along up/down and left/right bending directions. The rear ends of the bending wires 41u, 41d, 41l and 41r are connected to pulleys 42a, 42b configuring a motor unit 22 arranged in the operation portion 14, for example.

In the operation portion 14 are disposed the pulley 42a on which a wire connected with the both ends of the up/down direction bending wires 41u, 41d is wound, and the pulley 42b on which a wire connected with the both ends of the left/right direction bending wires 41l, 41r is wound.

The pulleys 42a, 42b are connected to a rotational axis of an UD motor 43a for up/down bending (driving) and a rotational axis of an RL motor 43b for left/right bending (also referred to shortly as the motors 43a, 43b), respectively, and rotated according to the rotation direction of the motors 43a, 43b which are rotatable normally and reversely.

The motors 43a, 43b configuring bending driving means in the up/down and left/right directions are controlled by the PC main body 7 connected to the motor unit 22, as shown in FIG. 7.

Thus, electric bending driving means is configured to electrically bend and drive the bending portion 18 by hauling and relaxing (pulling and pushing) the bending wires 41u, 41d, 41l, and 41r by the rotation of the pulleys 42a, 42b caused by the motors 43a, 43b.

The amount of bending of the bending portion 18 corresponds to the rotating amounts of the pulleys 42a, 42b generated by the rotation through the motors 43a, 43b. Therefore, the rotating amounts of the pulleys 42a, 42b are referred to as pulley angles.

The rotational angles (also referred to as motor angles) or the pulley angles of the motors 43a, 43b are detected by an up/down rotary encoder (UD encoder) 44a and a right/left rotary encoder (RL encoder 44b) which are attached to the rotational axes of the motors 43a, 43b, respectively, for example, as detecting means for detecting the rotational angle or the rotation position.

Encoder outputs from the UD encoder 44a and the RL encoder 44b are inputted to the PC main body 7 as shown in FIG. 7.

In the automatic bending control mode, the rotation of the motors 43a, 43b in the motor unit 22 is controlled such that the bending portion 18 is driven and bent in the direction of the target position based on the estimation result of the target position by the UPD apparatus 11 from the PC main body 7 side and the current position and direction of the (endoscope) distal end portion 10 side.

In addition, the PC main body 7 performs calculation processing of the target position which corresponds to the desired bending direction by image processing.

Note that the automatic bending control mode is a bending control mode for electrically performing bending control based on the image analysis result of the endoscopic image, as described later.

The typical automatic bending control mode includes a centering mode as a first bending control mode in which bending control is performed such that the luminal dark part is detected by the image analysis of the luminal dark part (that is, calculation of an image feature value) performed on the endoscopic image and the luminal dark part is captured at the center (of the endoscopic image), and a searching mode as a second bending control mode in which the luminal dark part is searched in a luminal dark part undetectable state or a state close thereto such that the direction in which the luminal dark part exists is estimated from history information of the past bending control and the endoscope distal end is directed in the estimated direction.

In other words, there are a centering mode as a bending operation mode for bending the bending portion 18 by setting the position of the luminal dark part as an insertion target based on the calculated image feature value and directing the distal end of the insertion portion to the position of the luminal dark part and a searching mode as a bending operation mode for estimating the present position of the luminal dark part based on the history information including the position of the luminal dark part which was calculated in the past and directing the distal end of the insertion portion in the direction of the estimated position.

Thus, in the present embodiment, the bending control mode is switched to the searching mode when the luminal dark part becomes undetectable ("disappearance or loss of the sight" of the luminal dark part) in the centering mode. Furthermore, in the present embodiment, bending control for more stable insertion is performed by switching between the centering mode and the searching mode according to preset switching conditions.

Furthermore, by changing the preset switching conditions according to a determination result as to whether the site of the lumen falls under the conditions for switching the switching conditions or the site is where the switching conditions should be switched, even if features and characteristics are different depending on the region (site) of the lumen into which the insertion portion is inserted, the insertion portion can be smoothly inserted into the deep part of the lumen.

Note that, when bending is performed by manual operation, according to the instruction values for bending the bending portion in an arbitrary bending direction of the up/down and the left/right directions which are given by the joystick 21 as bending instruction operation means provided on the operation portion 14, the rotation drive amounts of the motors 43a, 43b (corresponding to the pulley angles of the pulleys 42a, 42b) are controlled such that encoder outputs coincide with the instruction values, and the bending portion 18 is bent up to the instructed amount of bending.

To this end, the joystick 21 is provided, for example, with encoders, not shown, for detecting tilt operation amounts in the up/down direction and the left/right direction, thereby providing instruction information on the bending instruction value and the bending direction. In this case, the PC main body 7 just performs bending control such that the encoder outputs coincide with the instruction value. FIG. 7 shows a functional configuration of the PC main body 7. The endoscopic image signal from the processor 4 is stored as endoscopic image data in the memory 52 through the A/D conversion circuit 51 in the PC main body 7.

Furthermore, the information on the coordinates and direction of the coils from the UPD apparatus 11 is stored in the memory 52 through a coil information acquisition thread 53 as endoscope shape parameters, and more specifically, as data of the coil coordinate positions, the coil directions, and the distal end up-direction.

The endoscopic image data and endoscope shape parameter data are outputted to a main processing section (or a main thread) 55 configured of a CPU.

Note that the CPU may be configured to perform not only the processing of the main processing section 55 but also other processing such as the processing of an amount-of-bending control thread 56, as described later. Alternatively, the main processing section 55 shown in FIG. 7 may be configured to perform the processing of the amount-of-bending control thread 56.

The encoder outputs from the motor unit 22 of the endoscope 2 are inputted to the amount-of-bending control thread 56. The amount-of-bending control thread 56 stores the encoder outputs (that is, pulley angles) from the motor unit 22 as amount-of-bending parameters (for saving) in the memory 52 together with the data (information) at the time t.

The amount-of-bending parameters are stored together with other data in the ring buffer 58 as a storage section (memory section) for history information through the main processing section 55. With the elapse of the time t, data used for the past bending control is stored together with the past time t in the ring buffer 58 in an order of time (temporal sequence).

Specifically, data such as the (endoscope) distal end position, the direction thereof, the up-direction (or absolute amount of twist), the target position, and the bending angle (or pulley angle) are stored in the ring buffer 58 in the order of time t. Note that when the target position cannot be calculated, data of the target position and data of the bending angle related thereto are missing.

The ring buffer 58 used in the present embodiment includes memory portions M1, M2, ... Mn which are formed in a ring shape. After data are stored in the memory portions sequentially from the memory portion M1 to the memory portion Mn, the next data is overwritten in the first memory portion M1.

The data used for the past bending control and stored in the ring buffer 58 is used when a luminal dark part has disappeared from the endoscopic image and the luminal dark part cannot be detected in the automatic bending control mode, or the bending control mode is switched specifically to the searching mode according to the switching conditions to be described later.

In the searching mode, the past history information stored in the ring buffer 58 is referred to backward from the time when the luminal dark part disappeared, and the bending control information at the time when the luminal dark part was detected is read out, for example.

Then bending control is performed to bring the present bending control state back into the past bending control state where the luminal dark part was detected, thereby enabling the luminal dark part to be detected in the endoscopic image.

Hereinafter, the centering mode and the searching mode in the automatic bending control mode are generally referred to just as the operation mode, except for the case where these modes may be confused.

The data of the amount-of-bending parameters (for controlling), which was generated by the processing performed by the main processing section 55 and temporarily stored in the memory 52, is inputted to the amount-of-bending control thread 56.

The amount-of-bending parameters include set pulley angles as pulley angles for setting the present pulley angles to the target position direction. Note that, as the above-described amount-of-bending parameters (for saving), the amount-of-bending parameters (for controlling), which were generated by the processing performed by the main processing section 55, may be used (when the time difference between the two is small, the parameters have almost the same value).

As shown by the dotted lines in FIG. 7, when the amount-of-twist detecting unit 23 is used, the relative amount of twist detected by the amount-of-twist detecting unit 23 is stored in the memory 52 through an amount-of-twist acquisition thread 57, as data of the relative amount of twist which is one piece of the data of endoscope shape parameter, for example.

The amount-of-bending control thread 56 converts the calculated pulley angles into motor voltages (more specifically, the UD motor voltage value and the RL motor voltage value) and outputs the voltages to the UD motor 43a and the RL motor 43b of the motor unit 22.

The main processing section 55 outputs to the PC monitor 8 the information to be displayed through a video circuit 59a, and displays the information which should be presented for the operator, such as distal end passing target position detection or the amount-of-bending parameters, which will be described later.

In addition, a user such as the operator 20 can provide instructions for mode selection related to the bending control mode and for data input and the like to the main processing section 55 through the keyboard 59b, for example. Note that the mode selection and the like may be performed by a switch, a mouse, or other input devices instead of the keyboard 59b.

In addition, in the present embodiment, for example, a nonvolatile memory includes a switching condition/change information storage section 60 for storing information corresponding to the switching conditions for switching among a plurality of operation modes, and information on change of switching conditions, based on which the switching conditions themselves are changed (shortly referred to as switching condition/change information).

When the automatic bending control mode is selected, the main processing section 55, as described later, switches among the operation modes (for example, switching between the centering mode and the searching mode) with reference to the information on the switching conditions for switching among the plurality of operation modes, which is stored in the switching condition/change information storage section 60, and when the region into which the endoscope distal end is inserted is changed due to movement (of the endoscope distal end), the main processing portion 55 changes (switches) the switching conditions themselves such that the switching conditions are suitable for the bending control of the site (region) to which the endoscope distal end was moved.

In addition, in the present embodiment, the endoscope distal end is actually inserted into the insertion passage (insertion path) of the luminal organ such as large intestine toward the deep part of the insertion path, so that the switching conditions are changed depending on a plurality of sites of the insertion path (hereinafter path values) PI (I=1, 2, etc.) at which the endoscope distal end is located or the insertion length L. The switching conditions are changed depending on the path values PI, thereby capable of appropriately respond to the case where the feature value or the feature value parameter of the luminal dark part in the endoscopic image changes in the insertion path.

That is, the switching condition/change information storage section 60 stores a path list 60a in which all the information related to the switching conditions of the operation modes (more specifically, feature value parameters) are listed as one set (in a broader sense, related to one another) in association with each of the path values PI.

The pieces of information corresponding to the switching conditions are switched or changed depending on each of the path values PI as an insertion site in the lumen (organ) at which the endoscope distal end is actually located in the insertion path, thereby facilitating the smooth insertion of the endoscope distal end toward the deep part of the lumen.

FIG. 8 shows a functional configuration of the main processing section 55.

As shown in FIG. 8, the main processing section 55 includes a function of an intra-image target position detecting section 55a that detects a target position based on luminal information in an endoscopic image, a function of an endoscope shape processing section 55b that detects a position and a direction of each part of the endoscope from the coil coordinates, and a function of an amount-of-twist calculating section 55c that calculates an absolute amount of twist from a relative amount of twist. Note that, as shown by the dotted lines, the amount-of-twist calculating section 55c performs the processing when the relative amount of twist is inputted.

The intra-image target position detecting section 55a detects, from the endoscopic image, the center position (or the gravity center position) of the luminal dark part corresponding to the running direction of the lumen in the endoscopic image, as two-dimensional position information.

The position of the luminal dark part is detected in consideration of the values such as pixel size and the focal point distance of the CCD 33. Based on the information of the position of the luminal dark part with respect to the distal end position of the insertion portion 9 at the time, the direction of the luminal dark part is detected as the insertion direction of the distal end of the insertion portion (endoscope distal end).

Furthermore, based on the two-dimensional position information of the luminal dark part, a three-dimensional position including a value in the depth direction of the luminal dark part is further calculated by the Shape From Shading method (abbreviated as SFS method) as a shape restoration method from shading, for example. The three-dimensional position information is used as information on the target position to which the distal end of the insertion portion 9 is to be oriented and introduced.

Note that the target position detected by the intra-image target position detecting section 55a is transformed into a target position of the world coordinate system by a coordinate system transforming section in the intra-image target position detecting section 55a.

The transformed target position is outputted to the amount-of-bending calculating section 55d that calculates an amount of bending. The amount-of-bending calculating section 55d receives the information on the position, direction, and velocity of each part of the endoscope from the endoscope shape processing section 55b. Note that when the target position cannot be detected by the intra-image target position detecting section 55a or when it is desirable to switch the operation mode, the operation mode is switched by an operation mode/switching condition determining section 55f to be described below, according to the preset switching conditions.

In addition, the amount-of-bending calculating section 55d receives the absolute amount of twist from the amount-of-twist calculating section 55c. The absolute amount of twist is not calculated when the amount-of-twist detecting unit 23 is not provided.

Based on the amount of twist detected by the amount-of-twist detecting unit 23, the rotation angle at which the insertion portion 9 is rotated around the axis thereof is detected.

Note that, even when the amount-of-twist detecting unit 23 is not provided, by detecting the positions of the coils 36a and 36a' shown in FIG. 4, (the up-direction can be detected, and instead of using the amount of twist) the bending direction (or the orientation around the axis) of the endoscope distal end can be calculated.

In the present embodiment, the main processing section 55 further includes an image feature value calculating section 55e as intra-lumen insertion state estimating means that detects or estimates from an endoscopic image the intra-lumen insertion state (or insertion region state) of the endoscope distal end in the endoscopic image.

The image feature value calculating section 55e mainly calculates the image feature values related to the luminal dark part in the endoscopic image. More specifically, as shown in FIG. 11, the image feature value calculating section 55e calculates the image feature values including a luminal dark part distance D, a halation pixel ratio a, a dark-part pixel ratio b, an (luminal dark part) elliptic major axis/minor axis ratio r, and an edge line maximum length e.

In the present embodiment, the luminal dark part distance D represents the distance from the endoscope distal end to the luminal dark part. The luminal dark part distance D is calculated by transforming the two-dimensional information of the luminal dark part acquired from the endoscopic image into the three-dimensional information by means of the SFS method.

In addition, the halation pixel ratio a represents the proportion of the halation pixels to the total pixels in the endoscopic image. The halation pixels are pixels in which (signal) pixel values (pixel levels or luminance levels) of signal pixels of R, G, B components constituting the endoscopic image are determined to be equal to or larger than a saturation value or a threshold close to the saturation value, for example.

In addition, the dark-part pixel ratio b represents the proportion of the pixels determined to be the dark part to the total pixels in the endoscopic image. The dark-part pixels are pixels in which the pixel values of signal pixels of R, G and B components are equal to or smaller than a black level or a threshold close to the black level, for example.

Furthermore, since the luminal dark part is usually detected as an elliptic shape, the (luminal dark part) elliptic major axis/minor axis ratio r represents the ratio of the major axis to the minor axis of the ellipse in the case where the luminal dark part is regarded as the ellipse.

The edge line maximum length e is the maximum length of the edge line extracted when edge extraction is performed on the endoscopic image.

In addition to the values described above, presence or absence of an edge corner (See FIG. 15) is also one of the image feature values.

The image feature value calculating section 55e outputs the calculated image feature values to the operation mode/switching condition determining section 55f in the amount-of-bending calculating section 55d, for example.

Note that the information related to the luminal dark part in the image feature values calculated by the image feature value calculating section 55e may be sent to the intra-image target position detecting section 55a and the intra-image target position detecting section 55a may calculate the target position using the information.

In addition, the operation mode/switching condition determining section 55f receives also the endoscope shape feature value calculated by an endoscope shape feature value calculating section 55g. The endoscope shape feature value calculating section 55g calculates the endoscope shape feature value based on the information on the coordinates of the coils.

Specifically, the endoscope shape feature value is the insertion length L as shown in FIG. 11. The insertion length L can be calculated based on the distance from the position of the insertion entrance of the large intestine and the like to the positions of the coordinates of the coils provided in the endoscope distal end along the endoscope shape, for example.

Figure 16B:
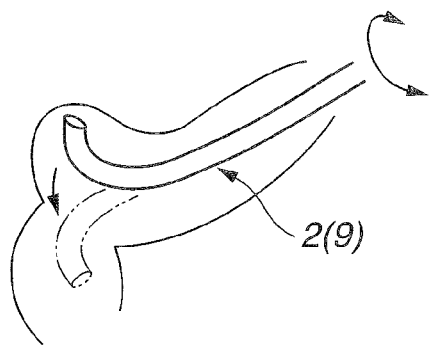
FIG. 16B is an illustration diagram illustrating a rotation mode.

In addition to the above, when the operation modes to be described later with reference to FIG. 16A or FIG. 16B are taken into consideration, the current amount of bending of the bending portion 18 and the amount of twist of the insertion portion 9 per unit time may be set as the endoscope shape feature values.

The operation mode/switching condition determining section 55f compares the calculated image feature values and the endoscope shape feature value with the parameter values of the information of the path list 60a (in this case, the information on the switching conditions) and determines whether or not to switch the operation mode based on the comparison result. Note that the determination in this case is performed mainly based on the calculated image feature values.

In addition, the operation mode/switching condition determining section 55f compares the calculated image feature values and the endoscope shape feature value with the parameter values of the information on switching condition change and determines whether or not to switch the switching conditions themselves.

In this case, the determination is performed mainly based on the calculated endoscope shape feature value. The switching condition change is set in order to appropriately respond to the feature value of the luminal dark part and the feature of the luminal organ itself (for example, the feature of the site at which the luminal organ is greatly flexed or deformable compared with other sites), when the endoscope distal end is inserted into the luminal organ.

Based on the determination result by the operation mode/switching condition determining section 55f, the operation mode is switched or the switching conditions themselves are changed. The operation mode/switching condition determining section 55f includes the functions of an operation mode switching section and a switching condition changing section.

Thus, the operation mode is switched and the switching conditions of the operation modes are changed depending on the insertion site in the body cavity, thereby enabling bending control for facilitating the smooth insertion of the endoscope distal end toward the deep part of the body cavity.

In addition, in each of the operation modes, the amount-of-bending calculating section 55d calculates the current position and direction of the endoscope distal end based on the information on the position and direction of the endoscope distal end in the received information.

Furthermore, the amount-of-bending calculating section 55d calculates the current position and direction of the endoscope distal end, and thereafter calculates the bending angles as shown in FIG. 9 in order to bend the endoscope distal end from the current position and direction in the direction of the target position.

The calculated bending angles are outputted through the memory 52 to the amount-of-bending control thread 56 as set pulley angles. The amount-of-bending control thread 56 converts the set pulley angles to the motor voltages (UD motor voltage, RL motor voltage) and applies the voltages to the UD motor 43a and the RL motor 43b in the motor unit 22.

Then the UD motor 43a and the RL motor 43b are rotationally driven, and thereby the bending portion 18 is bent such that the endoscope distal end coincides with the direction of the target position.

FIG. 9 shows the bending angles ($\phi$, $\theta$) by the relationship with respect to the insertion portion 9. The left part of FIG. 9 shows the angle $\theta$ formed between the orientation (direction) of the endoscope distal end and the desired bending direction (that is, the direction of the target position). Furthermore, the front view of the distal end surface in the right part of FIG. 9 shows the angle $\phi$ formed between the up (U) bending direction and the desired bending direction.

FIG. 10 shows a functional configuration of the amount-of-bending control thread 56. Information on the bending angles ($\phi$, $\theta$) calculated by estimation is inputted to an absolute pulley angle converting section 56a. The absolute pulley angle converting section 56a converts the information on the bending angles ($\phi$, $\theta$) into information on the absolute target pulley angle (pulley angle) in the up/down direction and the absolute target pulley angle in the right/left direction perpendicular to the up/down direction.

The generated absolute target pulley angle in the up/down direction and absolute target pulley angle in the right/left direction are inputted to a motor voltage setting section 56b.

Based on the information on the absolute target pulley angle in the up/down direction and the absolute target pulley angle in the right/left direction and information on the current pulley angle detected by the UD encoder and the current pulley angle detected by the RL encoder, the motor voltage setting section 56*b* generates digital motor voltages by PID control.

The digital motor voltages are converted into analog motor voltages by an A/D conversion unit 56*c*, and thereafter the analog voltages are applied to the UD motor 43*a* and the RL motor 43*b*. Note that the PID control is a kind of Feedback control and is a method in which an input value is controlled by three elements, that is, deflection between an outputted value and a target value, integration of deflection, and differentiation of deflection.

FIG. 11 shows a detail of the feature value parameters for determining the switching conditions (used for switching among the operation modes) for smooth insertion of the endoscope 2 into a large intestine 61 in a case where the insertion target region is set in the large intestine 61 as shown in FIG. 12, for example, and for switching the switching conditions in accordance with the transition or change of the path values PI (here, I=1, 2 and 3).

Note that, for simplification, the switching among the operation modes will be described below by taking the switching between the centering mode and the searching mode as an example.

As shown in FIG. 11, as the feature values or the feature value parameters for determining the switching conditions, the luminal dark part distance D, the halation pixel ratio a, the dark-part pixel ratio b are used.

In addition, as the feature values or the feature value parameters for determining the conditions in the case where the switching conditions are changed according to the transition of the path values PI, the insertion length L (luminal dark part elliptic) major axis/minor axis ratio r, the edge line maximum length e, the presence of edge corner are used.

The former switching conditions are changed according to the transition of the path values PI, thereby enabling the bending control for insertion to be performed in the operation mode also in the next path value P (I+1) after the transition, under the appropriate switching conditions (of the operation mode).

More specifically, as shown in FIG. 12, the switching conditions for the path value P1 are set in a rectum 62*a*, the switching conditions for the path value P2 are set in a sigmoid colon 62*b*, and the switching conditions for the path value P3 are set in a descending colon 62*c*. The switching conditions for each of the path values PI are determined by the comparison with the feature value parameters as described below.

The switching conditions (between the operation modes) for the path value P1 are as follows.
Centering mode: (when satisfying the conditions of) D>D1, a<a1, b<b1
Searching mode: (when satisfying the conditions of) D≦D1, a≧a1, b≧b1

The switching conditions (between the operation modes) for the path value P2 are as follows.
Centering mode: (when satisfying the conditions of) D>D2, a<a2, b<b2
Searching mode: (when satisfying the conditions of) D≦D2, a≧a2, b≧b2

The switching conditions (between the operation modes) for the path value P3 are as follows.
Centering mode: (when satisfying the conditions of) D>D3, a<a3, b<b3
Searching mode: (when satisfying the conditions of) D≦D3, a≧a3, b≧b3

In addition to the above, when the target position cannot be calculated, the operation mode is switched to the searching mode. Note that, the switching conditions described above are shown as one example. The switching conditions are not limited thereto (only one of the plurality of feature value parameters D, a and b may be adopted).

Furthermore, the switching conditions for the path value P1 are switched to the switching conditions for the path value P2, when L>L1 and r<r1 are satisfied. The switching conditions for the path value P2 are switched to the switching conditions for the path value P3, when L>L2 and e>e2 are satisfied.

The switching conditions for the path value P3 are switched to the switching conditions for the path value after the path value P3, when L>L3 and the presence of the edge corner are satisfied. In the present embodiment, the above-described feature value parameters for determining the switching conditions and the feature value parameters for changing the switching conditions are in association with each other as a set as the path list 60*a*.

Note that the luminal dark part distance D, the halation pixel ratio a, the dark-part pixel ratio b, the insertion length L, the major axis/minor axis ratio r, and the edge line maximum length e have the magnitude relations in the path values, as shown in the right-most columns in FIG. 11. That is, D3>D1=D2, a2=a3<a1, b1=b3<b2, L1<L2<L3, r1<1.4, e2<image width×0.8.

Note that the switching conditions may be simplified, and switching may be performed only using the insertion length L.

The supplementary descriptions on the luminal dark part distance D and the like are as follows.

As for the luminal dark part distance D, among the rectum 62*a* at the path value P1 to the descending colon 62*c* at the path value P3, the descending colon 62*c* is substantially linear, and therefore the luminal dark part distance D3 is generally long. In other regions, even if the luminal dark part distance D1 or D2 is short, there is a case where the situation does not mean "disappearance or loss of the sight" of the luminal dark part.

As for the halation pixel ratio a, since the flexion angle is steep (large) in the rectum 62*a* at the path value P1, the endoscope distal end is likely to face the intestinal wall of the rectum at a right angle with respect to the intestinal tract, and therefore, the halation pixel ratio a1 tends to be high.

In contrast, in other regions, at the time of "disappearance or loss of the sight" of the luminal dark part, the halation pixel ratios a2, a3 are not so high.

As for the dark-part pixel ratio b, since the sigmoid colon 62*b* at the path value P2 has a lot of folds, a lot of dark parts (shadows of the folds) other than the luminal dark part as the target exist in the endoscopic image, and therefore the dark-part pixel ratio b2 becomes high. In contrast, in other regions, at the time of "disappearance or loss of the sight" of the luminal dark part, the dark-part pixel ratios b1 and b3 are not so high.

As for the insertion length L, as (the endoscope distal end is) inserted deeper from the rectum 62*a*, the insertion length becomes longer.

As for the major axis/minor axis ratio r, the value is equal to or larger than 1.0 according to the definition of the ratio. When the value is smaller than 1.4, the luminal dark part becomes substantially circular shape. The value 1.4 is a value empirically set.

In addition, as for the edge line maximum length e, when the edge line maximum length is longer than the value obtained by multiplying the image width by 0.8, the edge which appears on the screen is regarded as large enough. The value 0.8 is a value empirically set. In addition, when the edge is long, the folds appear on the screen, that is, the feature effective for determination of the sigmoid colon 62b is represented.

Next, the operation of bending control according to the present embodiment will be described with reference to FIG. 13.

In the first step S1, the main processing section 55 performs an initial setting. Next, in step S2, the main processing section 55 acquires coil information, that is, information on the positions of the coils. In the next step S3, the main processing section 55 calculates the distal end position and the distal end direction of the endoscope based on the information on the positions of the coils. In the next step S4, the main processing section 55 acquires the image data of the endoscopic image.

In the next step S5, the main processing section 55 corrects distortion of the image data. Since the objective lens 32 has distortion and the like, distortion correction is performed on the image data of the endoscopic image acquired through the objective lens 32.

In the next step S6, the main processing section 55 detects, from the endoscopic image, the distal end passing target position for the endoscope distal end to be passed. Note that the distal end passing target position used here clearly represents the meaning as the target position through which the operator intends to actually pass the endoscope distal end, in the state of the current position (and direction) of the endoscope distal end. The detection of the distal end passing target position will be more detailed later with reference to FIG. 14.

Since the distal end passing target position detected in the step S6 is two-dimensional position information, in the next step S7, the main processing section 55 transforms the distal end passing target position into the position given by the three-dimensional coordinates using the above-described SFS method and the like.

In the next step S8, the main processing section 55 calculates target pulley angles corresponding to a bending direction in which the endoscope distal end is to be bent from the state of the current position of the endoscope distal end such that the direction of the endoscope distal end coincides with the direction of the distal end passing target position as the target position.

In the next step S9, based on the calculated target pulley angles, the main processing section 55 calculates motor voltages corresponding to the calculated pulley angles. Note that the calculation is performed as processing of the amount-of-bending control thread 56 in the exemplary configuration shown in FIG. 7. The calculated motor voltages are applied to the motors 43a and 43b of the motor unit 22, and the motors 43a and 43b are rotationally driven, thereby bending and driving the bending portion 18. After the processing in the step S9, the procedure returns to the processing in the step S2.

Next, description will be made on the detection processing of the distal end passing target position in the step S6, with reference to FIG. 14.

In the first step S11, the main processing section 55 calculates the image feature values (parameters) from the endoscopic image.

In the next step S12, the main processing section 55 calculates the endoscope shape feature values (parameters).

In the next step S13, the main processing section 55 performs determination processing as to whether or not to change the path list 60a.

In this case, when the processing in the step S13 is performed at first, the path value P1 is preset as the path list 60a in the initial setting in the step S1, for example. Specifically, the switching conditions (that is, the first switching conditions currently adopted) of the operation mode as shown in the path value P1 in FIG. 15 are set, and the conditions for transition (switching) to the next path value P2 (that is, the second switching conditions to which the first switching conditions is switched), which are stored in association with the first switching conditions as one set, are initially set.

When the endoscope distal end is inserted into the rectum 62a (the path value in this case is P1) shown in FIG. 12, it is determined that updating in the step S13 is not performed.

When such a determination result was acquired, in the next step S15, it is determined whether or not to move on to the searching mode based on the path list 60a (for example, path value P1).

On the other hand, when the endoscope distal end passes through the rectum 62a shown in FIG. 12 and moves on toward the sigmoid colon 62b which is located in a deeper part than the position of the rectum 62a, it is determined to fall under the conditions for transition (switching) from the path value P1 to the path value P2. That is, it is determined to update (change) the switching conditions.

In this case, as shown in the step S14, the feature value parameters for the next path value are acquired. That is, the switching conditions are changed to the second switching conditions. When the endoscope distal end moves from the rectum 62a toward the sigmoid colon 62b as described above, for example, the feature value parameters and the like corresponding to the path value P2 are acquired and the path list 60a is updated to the path value P2. The specific example of the path value P2 is shown in FIG. 15. Furthermore, when the endoscope distal end passes through the sigmoid colon 62b shown in FIG. 12 and moves on toward the descending colon 62c which is located in a deeper part than the position of the sigmoid colon 62b, it is determined to fall under the conditions for transition (switching) from the path value P2 to the path value P3. That is, it is determined to update the switching conditions. The specific example of the path value P3 is shown in FIG. 15.

After the processing in the step S14, the procedure moves on to the step S15. In the determination processing in the step S15, when it is determined to fall under the conditions for transition to the searching mode, the procedure moves on to step S16.

In the step S16, the amount-of-bending calculating section 55d reads out the past history information stored in the ring buffer 58, and performs bending control on the bending portion 18 so as to bring the endoscope distal end into a luminal dark part detectable state. When the endoscope distal end is brought into the luminal dark part detectable state, processing is performed for deciding (or calculating) the distal end passing target position for the endoscope distal end in the luminal dark part detectable state. Then the procedure moves on to the processing in the step S7 shown in FIG. 13.

On the other hand, in the determination processing in the step S15, when it was determined not to fall under the conditions for transition to the searching mode, that is, in a non-searching mode, the procedure moves on to the step S17. Note that the non-searching mode corresponds to the centering mode in the description above.

In the step S17, processing for deciding (or calculating) the distal end passing target position is performed in the non-searching mode. Then, the procedure moves on to the processing in the step S7 in FIG. 13.

According to such a bending control, the present embodiment allows the insertion operation of the endoscope distal end into the deeper part of the luminal organ to be smoothly performed, even when the luminal organ such as the large intestine 61 has different features depending on the insertion sites in the insertion path.

In other words, even if it is difficult to respond to the insertion target region or insertion target organ with only one set of switching conditions, the switching conditions are changed depending on the insertion sites in the insertion path which have different features, thereby enabling the bending control which allows the endoscope distal end to be smoothly inserted toward the deeper part.

In addition, in the present embodiment, according to the change in the features of the insertion target region (in response to the insertion of the endoscope distal end) according to the insertion length L from the entrance for insertion, the information on the switching conditions of operation modes and the information on changing of the switching conditions themselves are collectively switched, thereby facilitating the management of the switching between the operation modes and changing of the switching conditions.

Note that, in the above description, the centering mode as the first operation mode and the searching mode as the second operation mode are selected as operation modes and the switching between these modes was described. In addition to these modes, the fold push-in mode as shown in FIG. 16A or the rotation mode as shown in FIG. 16B may be selected as operation modes, for example, and these modes may be adopted.

As shown in FIG. 16A, for example, there is a possibility that the distal end side of the endoscope 2 is greatly bent at the region such as sigmoid colon 62b where the flexion amount of the intestinal tract is large and the shape of the intestinal tract changes because the region is not fixed.

In such a case, if the operation mode is set to the centering mode, the luminal dark part cannot be detected. Though it is possible to detect the luminal dark part by changing the operation mode to the searching mode, if the bending portion 18 is bent to the extent that the amount of bending is equal to or larger than a threshold as shown in FIG. 16A, for example, the operation mode may be switched to the fold push-in mode before switching to the searching mode.

In this case, the bending portion 18 is bent in a direction opposite to the current bending direction. That is, the bending portion 18 is bent in the direction shown by the arrow in FIG. 16A. The endoscope distal end side is brought into the shape shown by the two-dot-chain lines to facilitate the insertion into the deep part. Note that, in a case where the luminal dark part cannot be detected even after a set time has elapsed after the switching to the fold push-in mode, for example, the operation mode may be switched to the searching mode.

In addition, similarly, when the luminal dark part cannot be detected as shown in FIG. 16B in the state where the operation mode is set to the centering mode, the rotation mode may be allowed to be selected. The rotation mode is the manual operation mode in which the operator performs rotation operation of the endoscope 2.

When it is detected that the amount of bending of the bending portion 18 is equal to or larger than a certain threshold and the amount of twist of the endoscope 2 per unit time is equal to or larger than a threshold, or when the luminal dark part cannot be detected in the centering mode, the operator may select the rotation mode. Note that, in this case, the rotation operation which should be performed by the operator is displayed on the PC monitor 8 and the like. The operator performs the rotation operation as displayed, for example, as shown by the arrow, thereby bringing the endoscope distal end in the state where the luminal dark part can be detected more easily as shown by the two-dot-chain lines.

Figure 17:
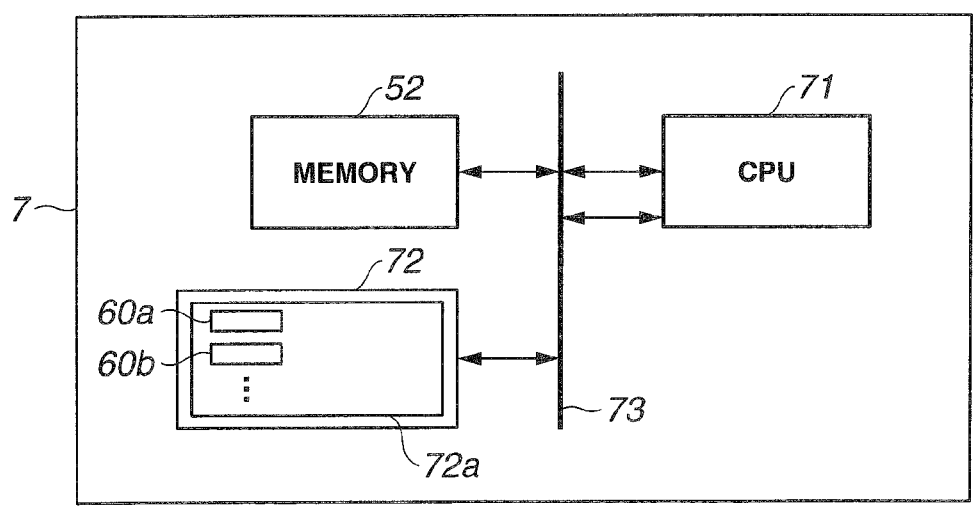
FIG. 17 is a block diagram showing a configuration in which the path lists set in advance corresponding to luminal organs and the like to be examined using an endoscope can be selected and used.

Note that the PC main body 7 may be configured as shown in FIG. 17, for example, as a modified example of the present embodiment. In the exemplary configuration shown in FIG. 17, when performing bending control using the above-described path list 60a, the CPU 71 which performs the processing of the main processing section 55 and the like in the PC main body 7 reads out the path list 60a from the path list information 72a stored in a hard disk (abbreviated as HDD) 72, for example, to use the path list 60a.

A plurality of path lists 60j (j=a, b, etc.) are prestored in the HDD 72 according to the luminal organ (for example, large intestine or small intestine) and the luminal region on which the endoscopic examination is performed. The CPU 71 selects and reads out from the HDD 72 the path lists 60j according to the luminal organ and luminal region on which the endoscopic examination is actually performed, and temporarily stores the read-out path lists in the memory 52 and the like, for example, to use the path lists. Note that the reference numeral 73 represents the bus.

According to the present modified example, similarly as in the first embodiment, it is possible to smoothly insert the endoscope into the lumina' organs, even when endoscopic examination is performed on different luminal organs.

Note that the path lists 60j may be changed and set depending on the body shape of the patient or medical procedure performed by the operator. For example, when the body shape of the patient is large or small, the feature value parameters may be changed and set depending on the body shape.

In addition, depending on the medical procedure performed by the operator, the operator may set the path lists 60j appropriate for the medical procedure. For example, in a case where the operator rapidly performs the insertion operation in the medical procedure, if the value of the luminal dark part distance D in the centering mode is set to be larger than the standard value, the probability of occurrence of the luminal dark part disappearance can be reduced.

Furthermore, the temporal data of the bending control in the case where the operator actually inserts the endoscope distal end into the large intestine 61 and the like is saved, and based on the saved data, the path lists 60j may be changed and set for performing smoother insertion.

(Second Embodiment)

Figure 18:
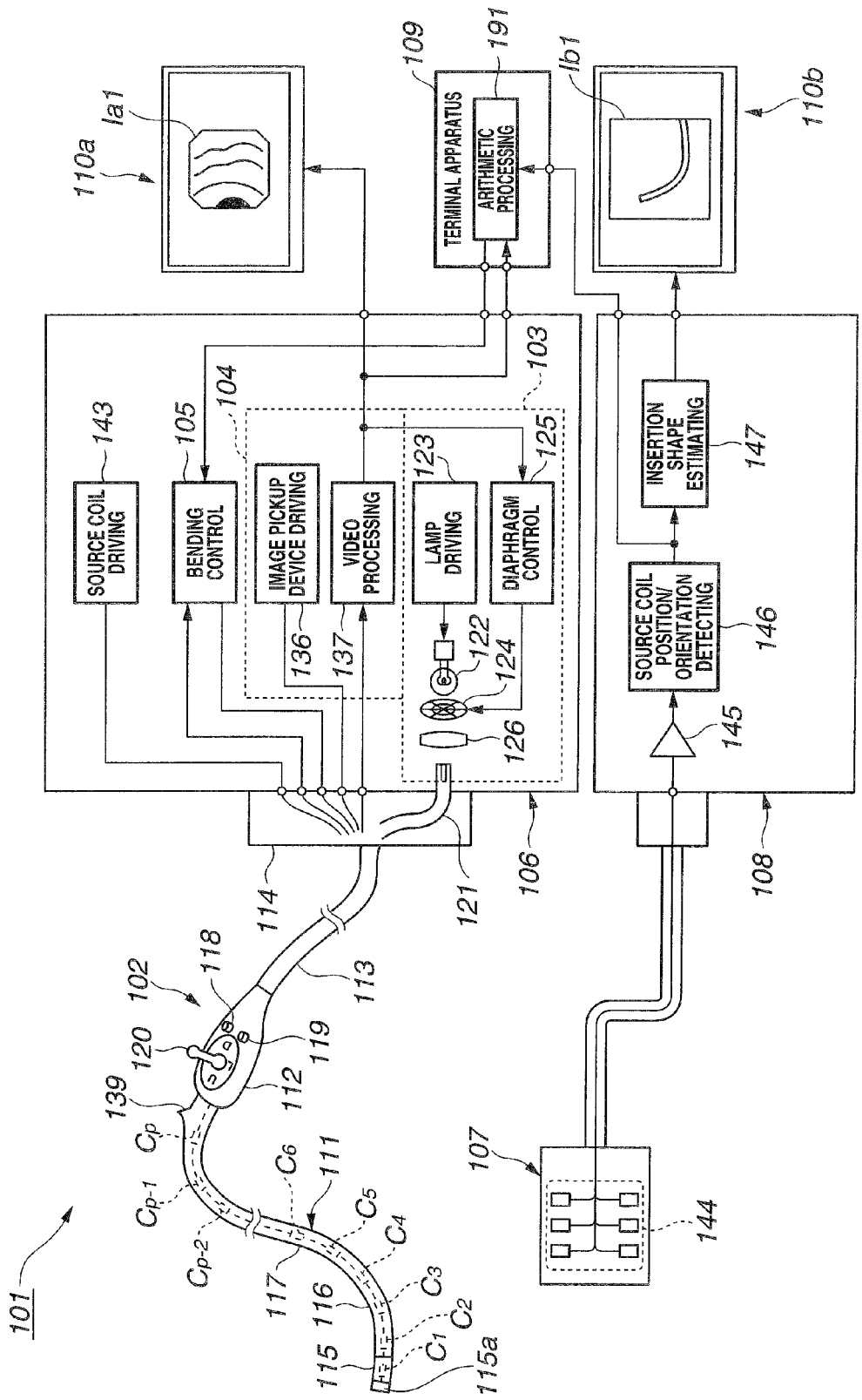
FIG. 18 is a view showing a configurational example of a main part of an endoscope system according to a second embodiment of the present invention.
Figure 19:
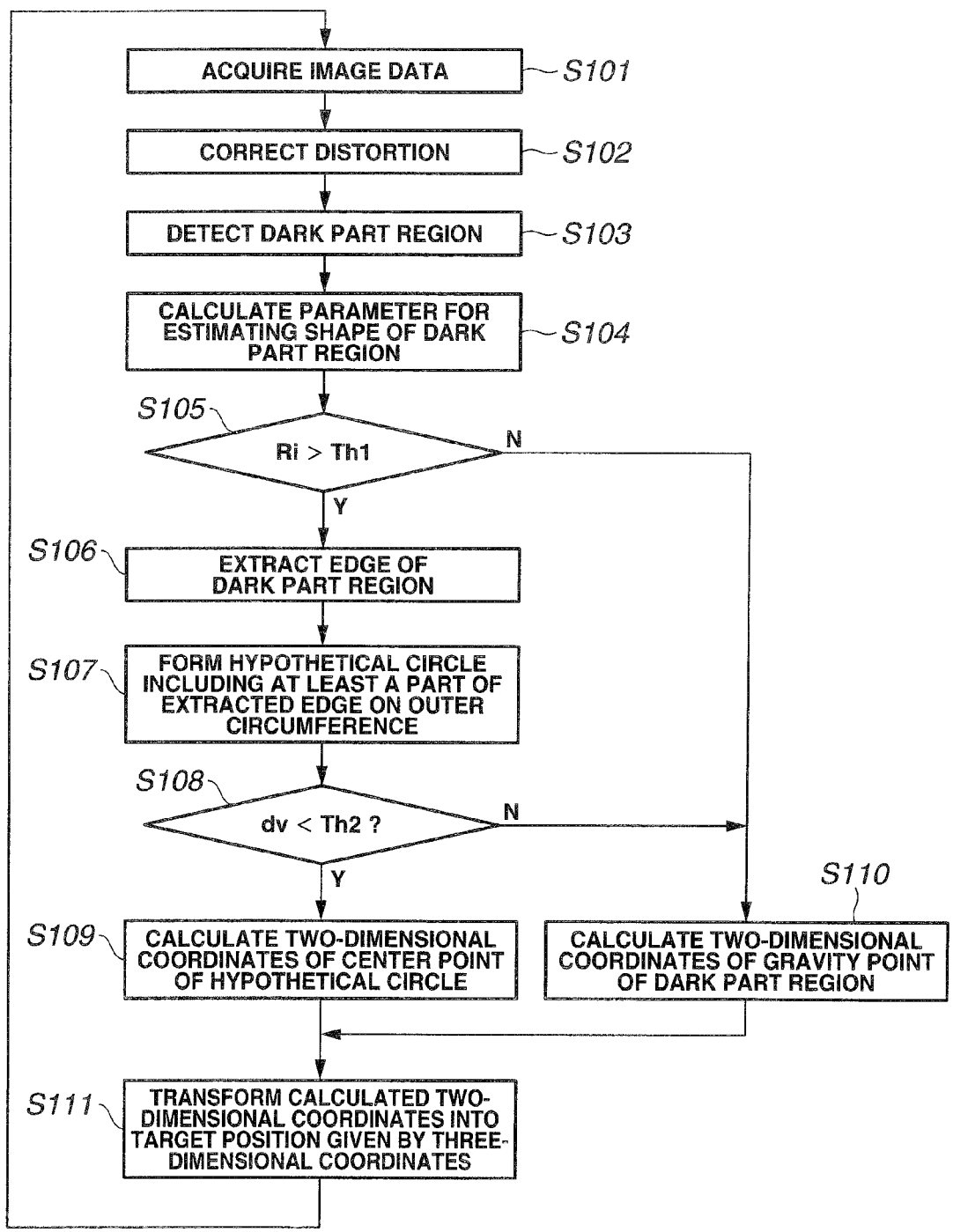
FIG. 19 is a flowchart showing an example of target position detecting processing performed in a terminal apparatus in FIG. 18.
Figure 20:
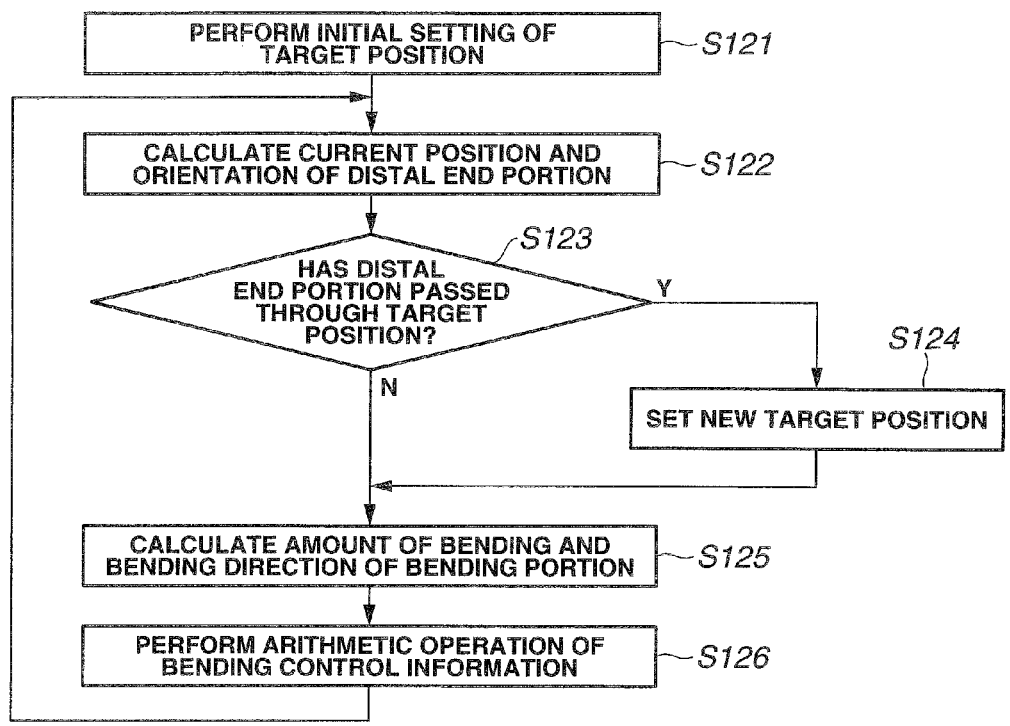
FIG. 20 is a flowchart showing an example of bending control setting processing performed in the terminal apparatus in FIG. 18.
Figure 21:
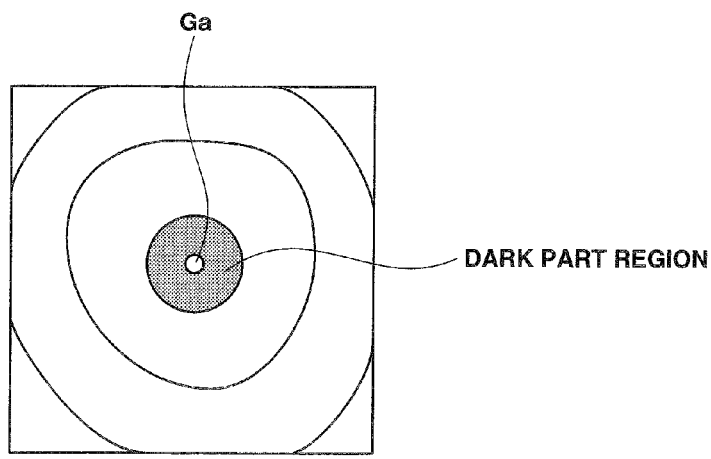
FIG. 21 is a view showing an example of a dark part region existing in image data.

FIGS. 18 to 23 relate to the second embodiment of the present invention. FIG. 18 is a view showing a configurational example of a main part of an endoscope system according to the second embodiment of the present invention. FIG. 19 is a flowchart showing an example of target position detecting processing performed in a terminal apparatus in FIG. 18. FIG. 20 is a flowchart showing an example of bending control setting processing performed in the terminal apparatus in FIG. 18. FIG. 21 is a view showing an example of a dark part region existing in image data.

Figure 22:
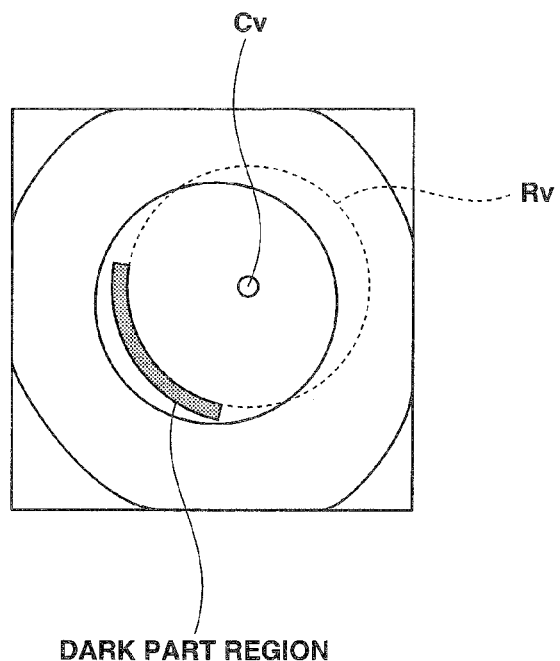
FIG. 22 is a view showing an example of a dark part region existing in image data, which is different from the example in FIG. 21.
Figure 23:
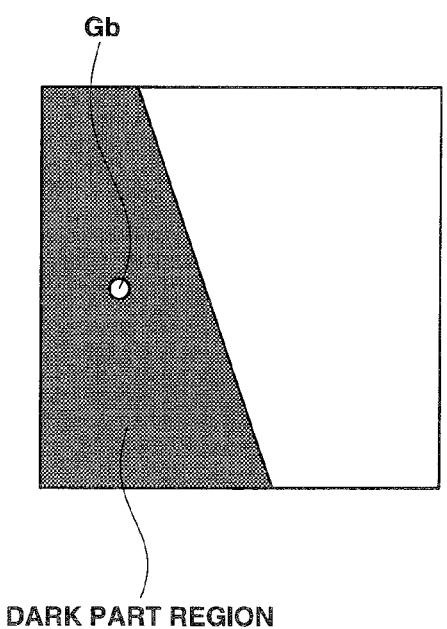
FIG. 23 is a view showing an example of a dark part region existing in image data, which is different from the examples in FIGS. 21 and 22.

FIG. 22 is a view showing an example of a dark part region existing in image data, which is different from the example in FIG. 21. FIG. 23 is a view showing an example of a dark part region existing in image data, which is different from the examples in FIGS. 21 and 22.

As shown in FIG. 18, an endoscope system 101 according to the second embodiment of the present invention includes: an endoscope 102 which is to be inserted into a body cavity of a patient as a subject and which picks up an image of a photographic subject in the body cavity; a processor 106 to and from which a connector 114 provided in the endoscope 102 is attachable and detachable; a sense coil unit 107 arranged around a bed on which the patient lies; an endoscope insertion shape detecting apparatus 108; a terminal apparatus 109; a monitor 110a, and a monitor 110b.

In addition, the processor 106 includes: a light source section 103 that supplies illumination light for illuminating a photographic subject as an image pickup object to the endoscope 102; a signal processing section 104 that generates a video signal by performing signal processing on an image pickup signal outputted from the endoscope 102 and outputs the generated video signal; a bending control section 105 that performs bending control on the endoscope 102; and a source coil driving section 143.

The endoscope 102 includes: an elongated insertion portion 111 to be inserted in the subject; an operation portion 112 provided at a rear end of the insertion portion 111; and a universal cord 113 extended from the operation portion 112. The connector 114 that is attachable and detachable to and from the processor 106 is provided at a rear end of the universal cord 113.

The insertion portion 111 includes: a rigid distal end portion 115 provided on a distal end side; a bending portion 116 connected to a rear end of the distal end portion 115; and a flexible tube portion 117 having flexibility that is provided between a rear end of the bending portion 116 and a front end of the operation portion 112. Furthermore, p-pieces of source coils $C_1, C_2, \ldots,$ and $C_p$ that generate magnetic fields corresponding to the source coil driving signals applied by the source coil driving section 143 are provided in the insertion portion 111 at substantially equal intervals.

The distal end portion 115 is provided with an image pickup section 115a including an objective optical system that forms an image of a photographic subject and an image pickup device that outputs the image of the photographic subject formed through the objective optical system as an image pickup signal.

The operation portion 112 is provided with a scope switch 118 that gives an instruction for acquiring a freeze image (still image), for example; a bending mode switching switch 119 that gives an instruction for switching the bending mode of the bending portion 116 to either the manual bending mode or the automatic bending mode, and a joystick 120 for bending operation for instructing the bending direction and the bending angle of the bending portion 116 when the manual bending mode is selected. In addition, at a portion which is on a rear end side of the flexible tube portion 117 and near the front end of the operation portion 112 is provided a treatment instrument insertion port 139 leading to a channel for treatment instrument, not shown, through which a treatment instrument or the like is insertable.

A light guide 121 that transmits the illumination light supplied from the light source section 103 to the distal end portion 115 is inserted in the insertion portion 111 and the like of the endoscope 102.

One end surface (incident end surface) of the light guide 121 is arranged protruding from the connector 114. Furthermore, the other end surface (light-emitting end surface) of the light guide 121 is arranged in the vicinity of an illumination optical system, not shown, provided in the distal end portion 115. According to such a configuration, in a state where the connector 114 is connected to the processor 106, the illumination light supplied from the light source section 103 passes through the light guide 121 and the illumination optical system, not shown, and thereafter illuminates the photographic subject as the image pickup object of the image pickup section 115a.

The light source section 103, for example, includes: a lamp 122 that emits illumination light which is white light; a lamp driving section 123 that supplies a power source required for driving the lamp 122; a diaphragm 124; a diaphragm control section 125 that increases and decreases the diaphragm amount (opening amount) of the diaphragm 124 based on the video signal outputted from the signal processing section 104; and a light condensing optical system 126 that condenses the illumination light passed through the diaphragm 124 and supplies the illumination light to the incident end surface of the light guide 121.

The diaphragm control section 125, for example, calculates the average brightness based on the luminance components of the inputted video signal, and thereafter appropriately changes the light amount of the illumination light passing through the diaphragm 124 by increasing and decreasing the diaphragm amount (opening amount) of the diaphragm 124 based on a difference value which is a value obtained by subtracting a reference value corresponding to the appropriate brightness from the average brightness.

The signal processing section 104 includes an image pickup device driving section 136 that outputs an image pickup device driving signal for driving the image pickup device provided in the image pickup section 115a, and a video processing section 137 that generates a video signal by performing signal processing on the image pickup signal outputted from the image pickup section 115a and outputs the video signal. According to this configuration, an endoscopic image Ia1 based on the video signal is displayed on the monitor 110a.

When the bending mode of the bending portion 116 is switched to the manual bending mode based on the instruction given by the bending mode switching switch 119, the bending control section 105 performs control to change the bending direction and the bending angle of the bending portion 116 based on the inclination direction and inclination amount of the joystick 120 for bending operation. In addition, when the bending mode of the bending portion 116 is switched to the automatic bending mode based on the instruction given by the bending mode switching switch 119, the bending control section 105 performs control to change the bending direction and the bending angle of the bending portion 116 based on the arithmetic operation result from the terminal apparatus 109.

The source coil driving section 143 is connected to the p-pieces of source coils $C_1, C_2, \ldots,$ and $C_p$ provided in the insertion portion 111, and sequentially applies an alternate current source coil driving signal to each of the source coils. As a result, an alternate current magnetic field is generated around each of the source coils provided in the insertion portion 111.

The sense coil unit 107 is provided with a sense coil group 144 that detects the magnetic field generated from each of the p-pieces of source coils $C_1, C_2, \ldots,$ and $C_p$ provided in the insertion portion 111 and outputs the detected magnetic fields as magnetic field detection signals.

The endoscope insertion shape detecting apparatus 108 having a function as a position detecting section includes: an amplifier 145 that amplifies the magnetic field detection signals outputted from the sense coil unit 107; a source coil position/orientation detecting section 146 that detects three-dimensional coordinate positions and orientations of the p-pieces of source coils $C_1, C_2, \ldots,$ and $C_p$ based on the magnetic field detection signals outputted from the amplifier 145, and outputs the detected three-dimensional coordinate positions and orientations as three-dimensional coordinate information; and an insertion shape estimating section 147 that estimates the insertion shape of the insertion portion 111 based on the three-dimensional coordinate information outputted from the source coil position/orientation detecting section 146, and outputs the estimated insertion shape as an insertion shape image signal. According to this configuration, an insertion shape image Ib1 of the insertion portion 111 based on the insertion shape image signal is displayed on the monitor 110b.

The terminal apparatus 109 includes an arithmetic processing section 191 composed of a CPU and the like. The arithmetic processing section 191 performs arithmetic operation related to the bending control performed when the bending mode of the bending portion 116 is the automatic bending mode, based on the video signal outputted from the video processing section 137 and the three-dimensional coordinate information outputted from the source coil position/orientation detecting section 146, and outputs the arithmetic operation result to the bending control section 105. Note that the specific content of the arithmetic operation performed in the arithmetic processing section 191 will be described later.

Next, description will be made on the working of the endoscope system 101. Note that description on the control in the case where the bending mode switching switch 119 is switched to the manual bending mode will be omitted below, and description will be mainly made on the control in the case where the bending mode switching switch 119 is switched to the automatic bending mode.

First, an operator connects and activates each part of the endoscope system 101, and thereafter inserts the insertion portion 111 of the endoscope 102 into a body cavity of a patient and switches the bending mode switching switch 119 to the automatic bending mode. In response to this, the image pickup section 115a in the endoscope 102 starts picking up an image of a photographic subject, and the source coils provided in the insertion portion 111 start to generate magnetic fields.

The image pickup signal outputted from the image pickup section 115a in association with the image pickup of the photographic subject is outputted to the processor 106, through the universal cord 113 and the connector 114, to be converted into a video signal in the video processing section 137, and thereafter inputted to the arithmetic processing section 191 in the terminal apparatus 109. In addition, the magnetic field detection signals outputted from the sense coil unit 107 in association with the generation of magnetic fields from the source coils provided in the insertion portion 111 are amplified by the amplifier 145, to be converted as the three-dimensional coordinate information of the source coils by the source coil position/orientation detecting section 146, and thereafter inputted to the arithmetic processing section 191 in the terminal apparatus 109.

The arithmetic processing section 191 in the terminal apparatus 109 performs target position detecting processing based on the video signal inputted thereto, thereby acquiring the three-dimensional coordinate position as a passing target of the distal end portion 115.

Here, the target position detecting processing performed by the arithmetic processing section 191 will be described.

The arithmetic processing section 191 in the terminal apparatus 109 acquires image data based on the video signal inputted thereto (step S101 in FIG. 19), and thereafter performs distortion correction on the image data (step S102 in FIG. 19). By performing the processing steps described above, the arithmetic processing section 191 acquires image data in which a monochrome portion is eliminated from the original image based on the inputted video signal.

The arithmetic processing section 191 as a dark part region detecting section uses the method disclosed in Japanese Patent Application Laid-Open Publication No. 2-203831, for example, to detect the dark part region in the image data acquired by the processing in step S102 in FIG. 19 (step S103 in FIG. 19). Note that the arithmetic processing section 191 may use other method as the method of detecting the dark part region in an image instead of the method disclosed in Japanese Patent Application Laid-Open Publication No. 2-203831.

After that, the arithmetic processing section 191 calculates a parameter for estimating the shape of the dark part region detected by the processing in the step S103 in FIG. 19 (step S104 in FIG. 19). Specifically, the arithmetic processing section 191 performs arithmetic operation using the following expressions (1) and (2) based on a primary moment m11 of the dark part region, a secondary moment m02 of the dark part region, and a secondary moment m20 of the dark part region, for example, and calculates a value of a ratio Ri between the major axis direction and minor axis direction in a case where an applicable ellipse is applied to the dark part region, as the parameter for estimating the shape of the dark part region.

$$msq = ((m20-m02) \times (m20-m02) + 4 \times m11 \times m11)^{1/2} \quad (1)$$

$$Ri = (((m20+m02)-msq)/((m20+m02)+msq))^{1/2} \quad (2)$$

The arithmetic processing section 191 determines whether or not the value of the ratio Ri calculated by the processing in step S104 in FIG. 19 is larger than a predetermined threshold Th1 (step S105 in FIG. 19).

When detecting that the value of the ratio Ri is equal to or smaller than the predetermined threshold Th1, the arithmetic processing section 191 estimates that the dark part region detected by the processing in the step S103 in FIG. 19 has the substantially circular shape as shown in FIG. 21, for example, and thereafter calculates the two-dimensional coordinates of a gravity point Ga of the dark part region (step S110 in FIG. 19). Note that, as the processing for calculating the two-dimensional coordinates of the gravity point of the dark part region, the arithmetic processing section 191 may perform the processing by regarding a centroid calculated according to sequence of points existing on the edge of the dark part region as the gravity point, or may calculate the gravity point using a 0th moment and the primary moment of the dark part region.

When detecting that the value of the ratio Ri is larger than the predetermined threshold Th1, the arithmetic processing section 191 judges that the dark part region detected by the processing in step S103 in FIG. 19 has another shape different from the substantially circular shape, and thereafter extracts the edge of the dark part region (step S106 in FIG. 19). Specifically, the arithmetic processing section 191 reduces the image data, and thereafter applies any one of Canny, Sobel, and Laplacian algorithms to the reduced image data to extract the edge of the dark part region.

Based on the edge of the dark part region extracted by the processing in the step S106 in FIG. 19, the arithmetic processing section 191 forms a hypothetical circle including at least a part of the edge on an outer circumference thereof (step S107 in FIG. 19). Note that, as the processing for forming the hypothetical circle, the arithmetic processing section 191 may perform processing based on a circle Hough transform, or processing to be described below.

The arithmetic processing section 191 detects shading gradient directions of the points on the edge of the dark part region, and after that, decides an approximate existing range of the center point of the hypothetical circle based on each of the shading gradient directions. Furthermore, the arithmetic processing section 191 calculates the distances from one point within the existing range to the respective points on the edge of the dark part region, and defines the summation of the distances as an evaluated value of the one point. The arithmetic processing section 191 calculates the evaluated values of all the points within the existing range and compares the calculated evaluated values one another, thereby forming the hypothetical circle with the point whose evaluated value is the smallest as the center point and with the length from the center point to the edge of the dark part region as the radius.

The arithmetic processing section 191 determines whether or not the diameter dv of the hypothetical circle formed by the processing in the step S107 in FIG. 19 is smaller than a predetermined threshold Th2 (step S108 in FIG. 19). Note that the threshold Th2 is assumed to be a value calculated based on the size of the image data acquired in the step S102 in FIG. 19, a diameter size of a normal lumen, or the data acquired in the past in substantially the same region of the same patient, for example.

When detecting that the diameter dv of the hypothetical circle is smaller than the predetermined threshold Th2, the arithmetic processing section 191 calculates the two-dimensional coordinates of the center point of the hypothetical circle (step S109 in FIG. 19). Specifically, the arithmetic processing section 191 calculates the two-dimensional coordinates of the center point Cv of the hypothetical circle Rv including on the outer circumference thereof at least a part of the edge of the dark part region, in the image data including the dark part region having a curved shape, as shown in FIG. 22, for example.

In addition, when detecting that the diameter dv of the hypothetical circle is equal to or larger than the predetermined threshold Th2, the arithmetic processing section 191 calculates the two-dimensional coordinates of the gravity point of the dark part region (step S110 in FIG. 19). Specifically, the arithmetic processing section 191 calculates the two-dimensional coordinates of the gravity point Gb of the dark part region in the image data including the dark part region having a shape which is neither the substantially circular shape nor the curved shape, as shown in FIG. 23, for example.

After that, the arithmetic processing section 191 as a target position setting section transforms the two-dimensional coordinates of any one of the center point Cv, the gravity point Ga, and the gravity point Gb calculated by the processing up to the tep S110 in FIG. 19 into the target position given by the three-dimensional coordinates by using the Shape From Shading method and the like (step S111 in FIG. 19), and thereafter repeats the series of processing steps from the step S101 again.

That is, when detecting the existence of the dark part region having a substantially circular shape as shown in FIG. 21, for example, in the above-described target position detecting processing, the arithmetic processing section 191 regards that the dark part region is generated by the lumen, and sets the three-dimensional coordinate position as the target such that the distal end portion 115 passes through the substantially the center portion of the lumen.

Furthermore, when detecting the existence of the dark part region having the curved shape as shown in FIG. 22, for example, in the above-described target position detecting processing, the arithmetic processing section 191 regards that the dark part region is generated by the folds and the like of the wall surface of the lumen and set the three-dimensional coordinate position as the target such that the distal end portion 115 is prevented from moving to the wall surface side and the distal end portion 115 passes through the position in the lumen where the distal end portion 115 is supposed to pass.

Meanwhile, the arithmetic processing section 191 performs a bending control setting processing for setting a content of control performed with respect to the bending portion 116 in the automatic bending mode, in parallel with the above-described target position detecting processing.

Now, description will be made on the bending control setting processing performed by the arithmetic processing section 191.

The arithmetic processing section 191 performs the above-described target position detecting processing for performing the initial setting of the target position for the distal end portion 115 to be passed at the timing immediately after the bending mode switching switch 119 is switched to the automatic bending mode (step S121 in FIG. 20).

In addition, the arithmetic processing section 191 calculates the current position and orientation of the distal end portion 115 based on the three-dimensional coordinate information outputted from the source coil position/orientation detecting section 146 (step S122 in FIG. 20).

After that, the arithmetic processing section 191 compares the current position and orientation of the distal end portion 115 calculated in the processing in the step S122 in FIG. 20 with the target position for the distal end portion 115 to be passed, thereby determining whether or not the distal end portion 115 has passed through the target position (step S123 in FIG. 20).

When detecting that the distal end portion 115 has passed through the target position, the arithmetic processing section 191 performs the above-described target position detecting processing again in order to set a new target position (step S124 in FIG. 20). In addition, when detecting that the distal end portion 115 has not passed through the target position, the arithmetic processing section 191 retains the target position and continues the processing.

After performing the processing in the step S123 or the step S124 in FIG. 20, the arithmetic processing section 191 calculates the amount of bending and the bending direction of the bending portion 116 such that the distal end portion 115 passes through the set target position (step S125 in FIG. 20). Note that, in the present embodiment, the arithmetic processing section 191 may calculate the amount of bending and the bending direction of the bending portion 116 by using different calculation methods depending on the shapes (substantially circular shape, curved shape or other shape) of the dark part region detected by the above-described target position detecting processing.

The arithmetic processing section 191, as a bending control information calculating section, performs arithmetic operation of the bending control information required for actually bending the bending portion 116, based on the amount of bending and the bending direction of the bending portion 116 calculated by the processing in the step S125 in FIG. 20 (step S126 in FIG. 20), and outputs the arithmetic operation result to the bending control section 105. After that, the arithmetic processing section 191 repeatedly performs a series of processing steps from the step S122 in FIG. 20 again.

Note that, when the bending portion 116 is composed of a plurality of bending pieces connected to one end side of the wire and configured to be capable of changing the bending state thereof according to tension or relaxation of the wire caused by the rotational driving of the motor, for example, the above-described bending control information is assumed to be shown as information related to the angles of the pulleys connected to the motor and the driving voltages applied to the motors. In addition, when the bending portion 116 has an alternative configuration other than the above-described configuration, for example, the above-described bending control information is assumed to be shown as information according to the alternative configuration.

The bending control section 105 is capable of performing, in the automatic bending mode, a control with respect to the bending portion 116 such that the distal end portion 115 always passes through the target position set in the above-described target position detecting processing, based on the arithmetic operation result outputted from the arithmetic processing section 191 in the terminal apparatus 109.

As described above, the endoscope system 101 according to the present embodiment is configured to be capable of controlling the endoscope bending portion such that the position and the orientation of the endoscope distal end portion is located at the position and oriented in the direction in accordance with the insertion operation of the endoscope insertion portion in the automatic bending mode. According such a configuration, the endoscope system 101 according to the present embodiment can facilitate the insertion operation of the endoscope regardless of the knowledge or the experience of the person who actually operates the endoscope.

(Third Embodiment)

Figure 24:
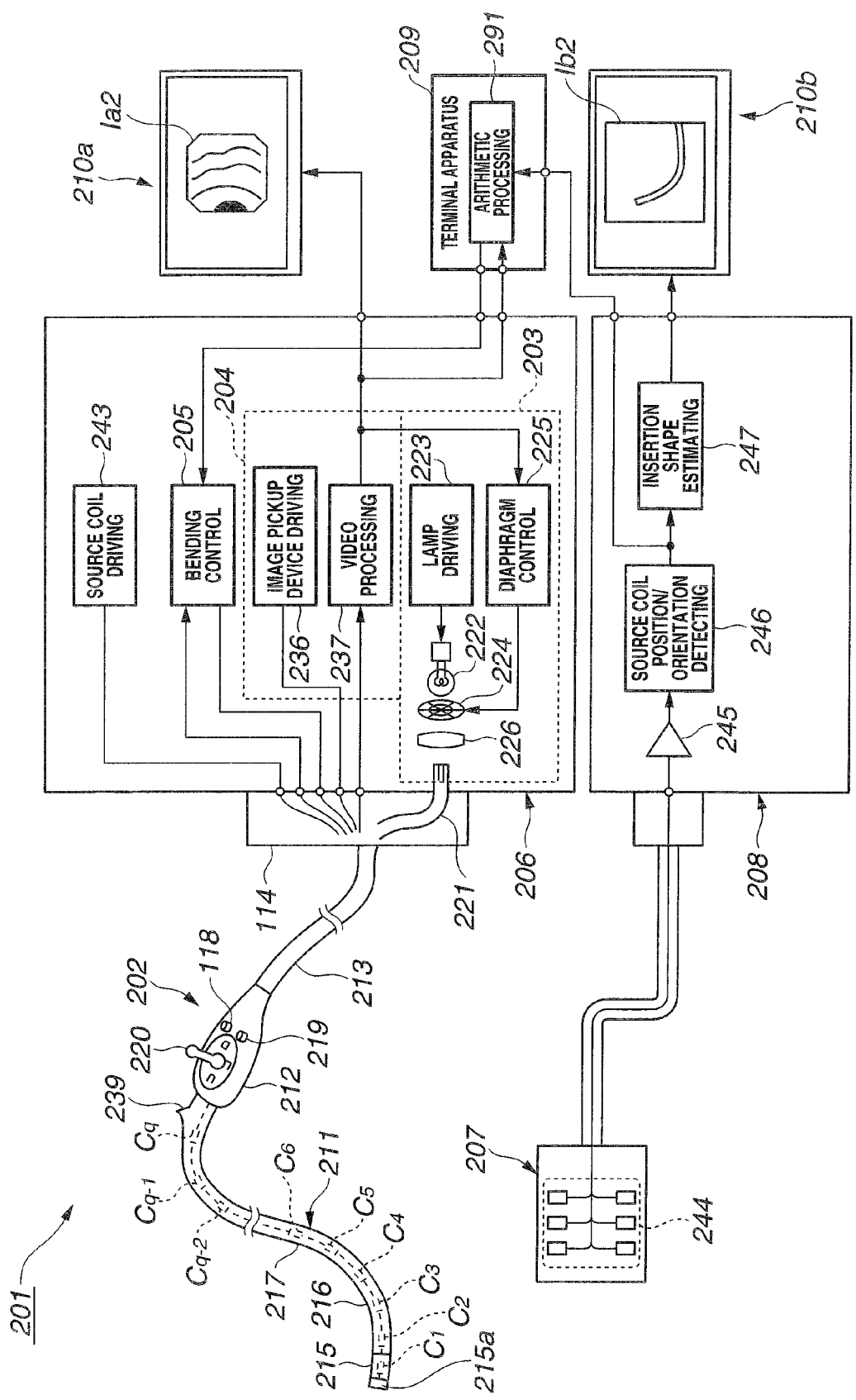
FIG. 24 is a view showing a configurational example of a main part of an endoscope system according to a third embodiment of the present invention.
Figure 25:
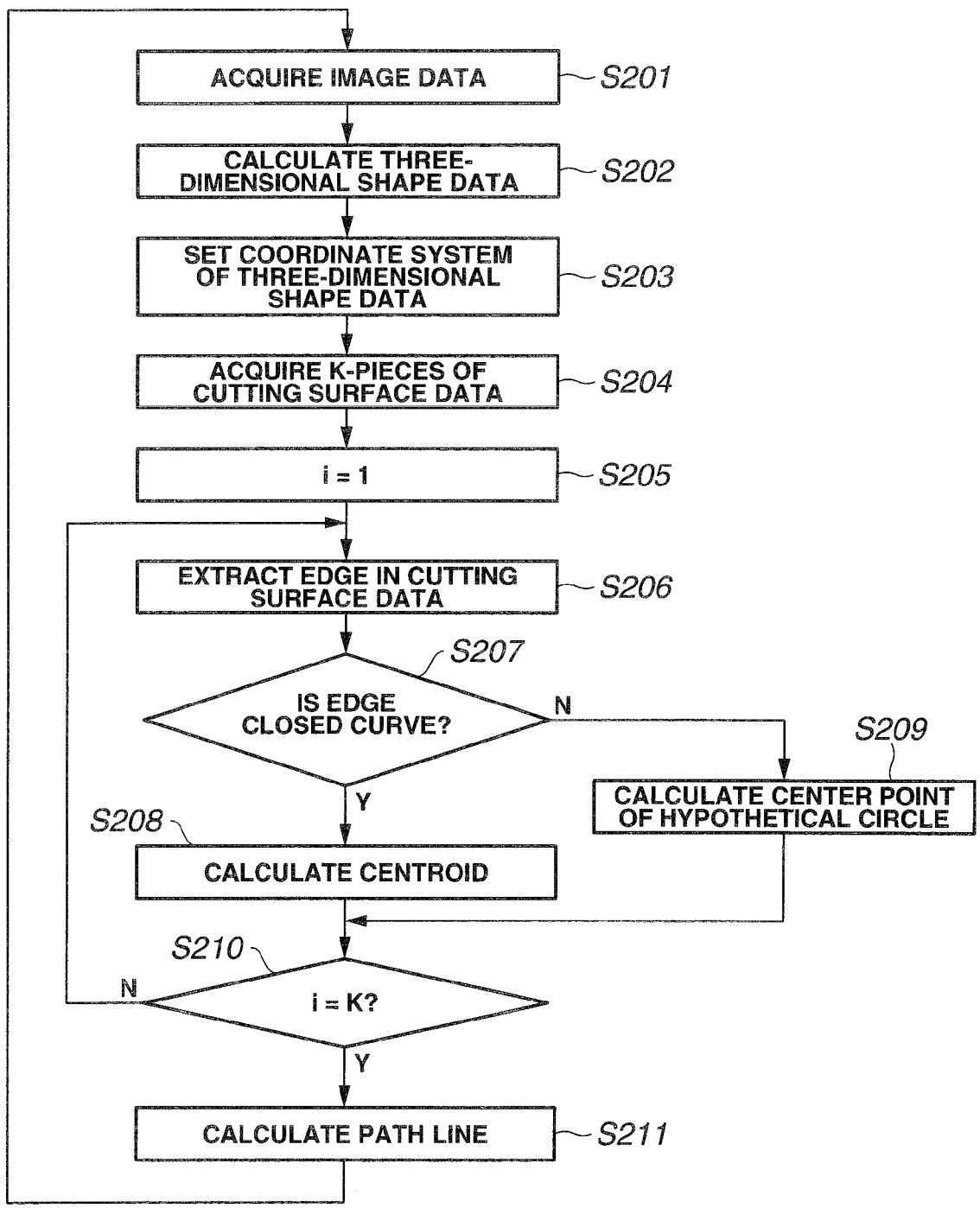
FIG. 25 is a flowchart showing an example of processing performed for setting a path for a distal end portion to be passed.
Figure 26:
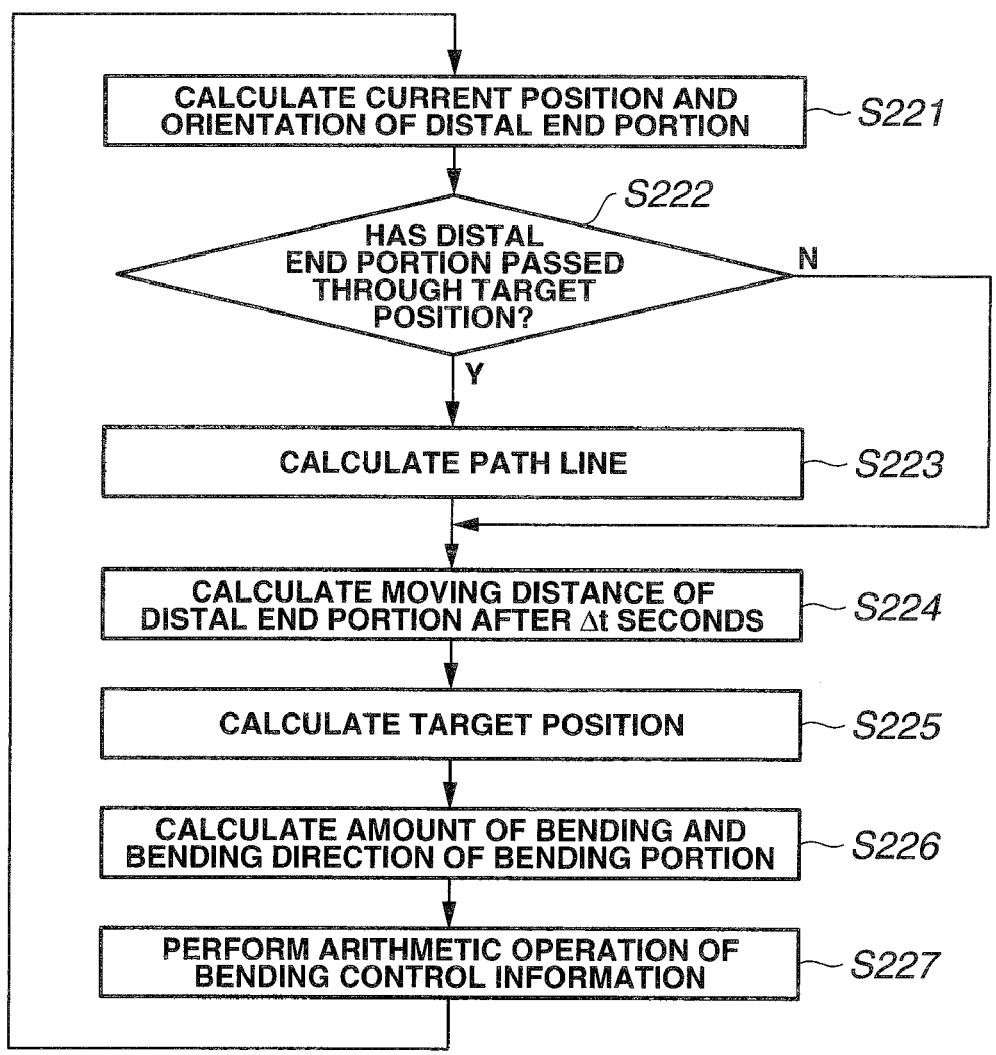
FIG. 26 is a flowchart showing an example of processing performed for setting a content of bending control performed with respect to the bending portion.
Figure 27:
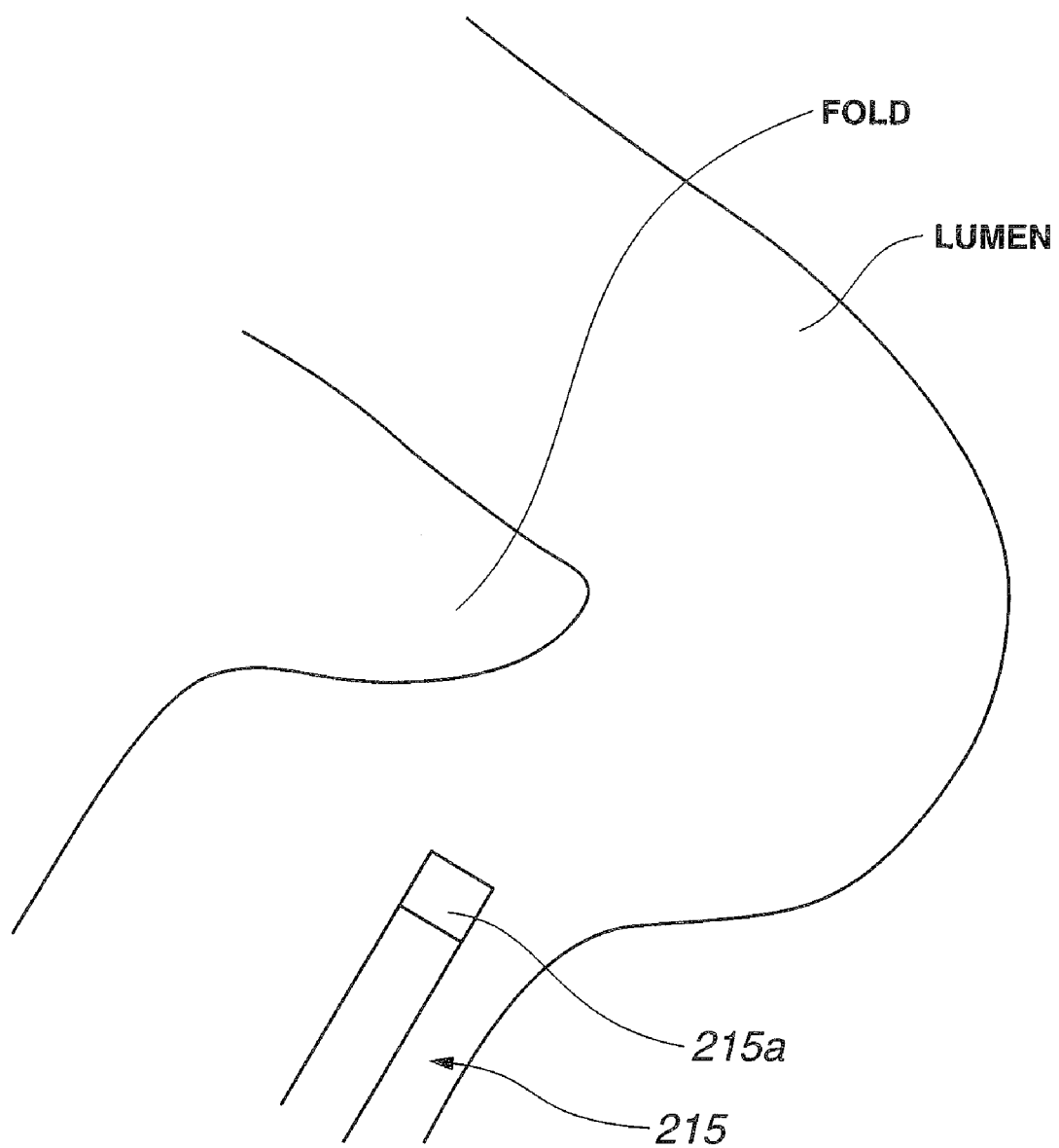
FIG. 27 is a view showing an example of a shape of a lumen in the vicinity of the current position of the distal end portion.
Figure 28:
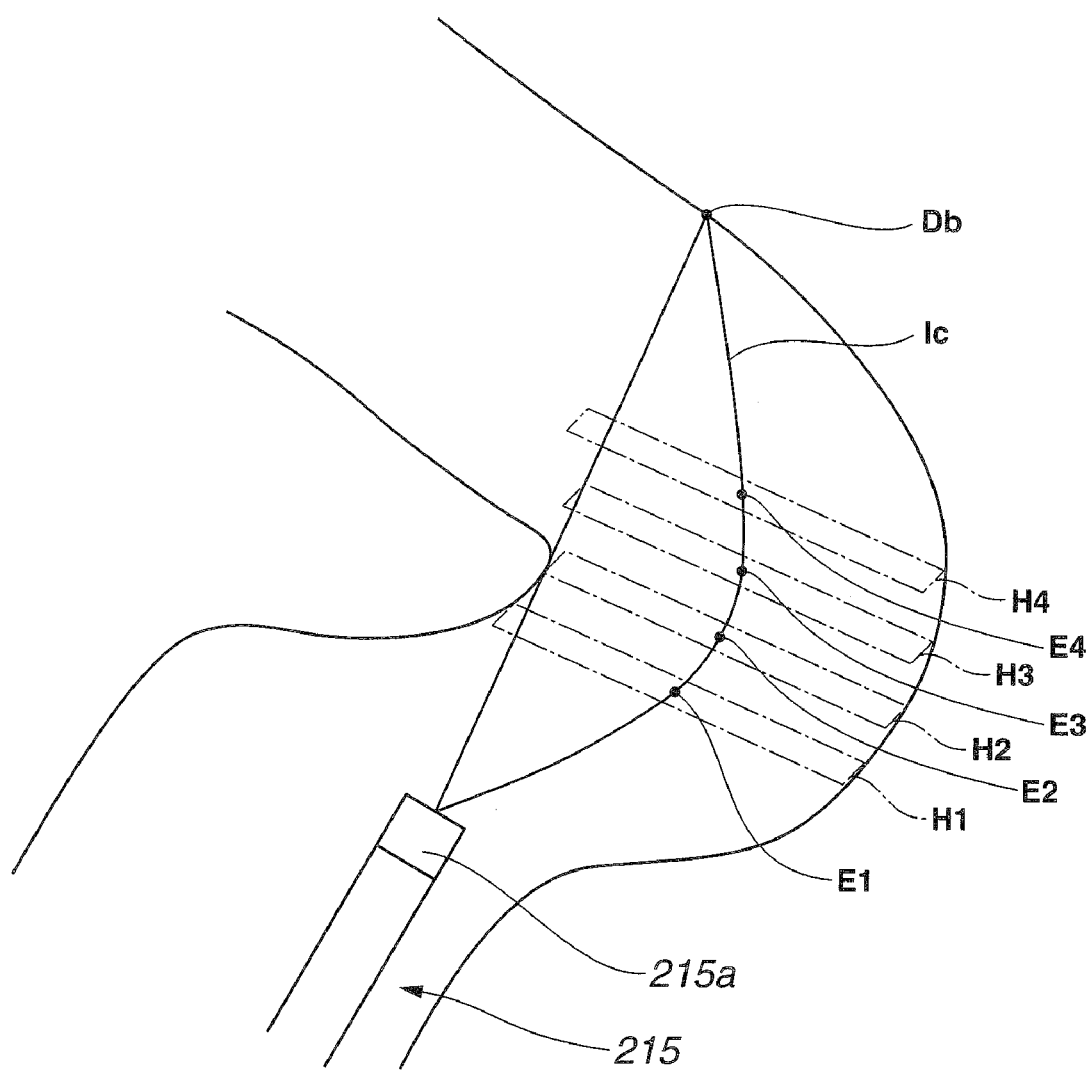
FIG. 28 is a schematic diagram related to a brief overview of the processing shown in the flowchart in FIG. 25.
Figure 29:
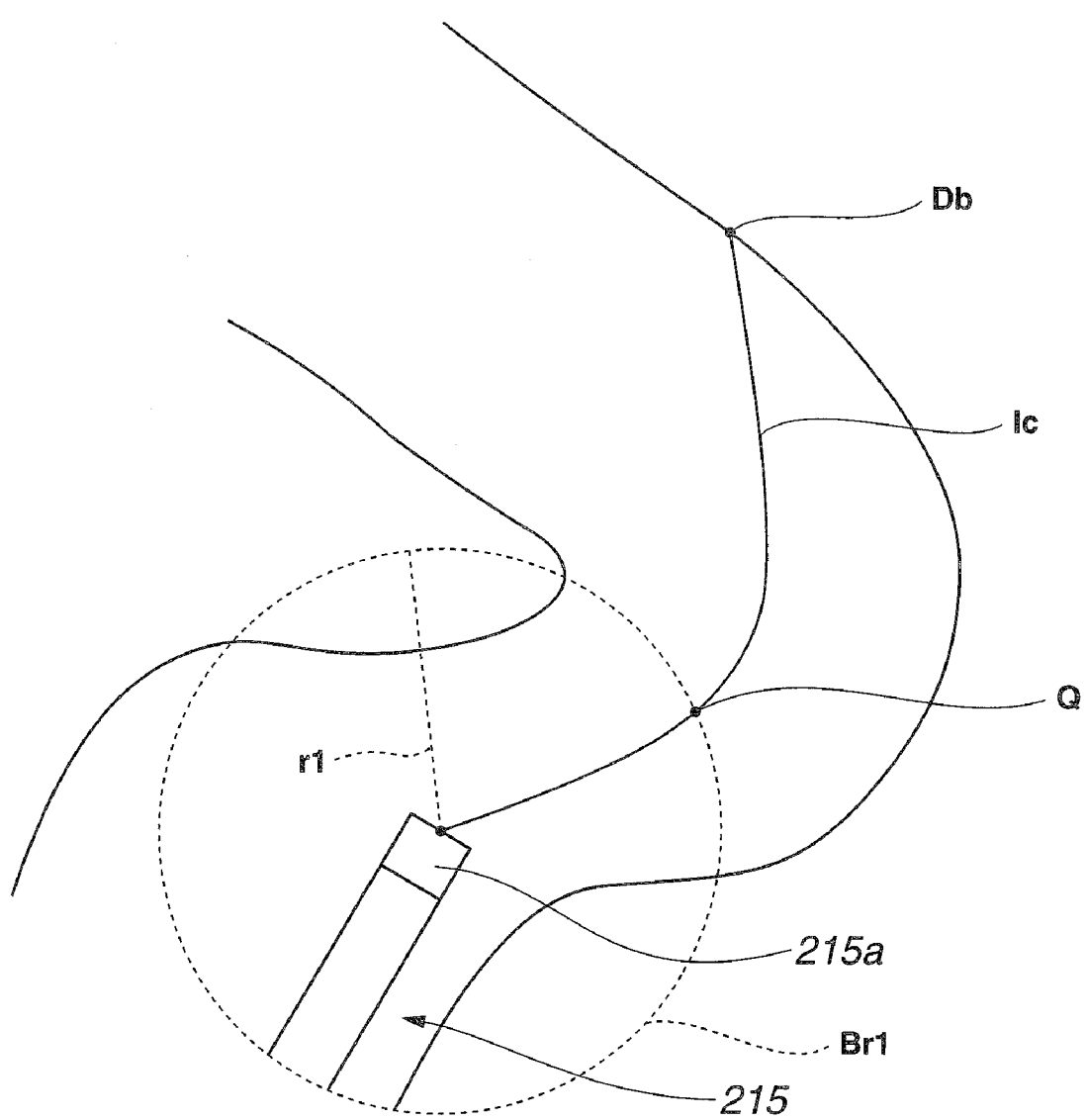
FIG. 29 is a view showing an example of processing of calculating a target position for the distal end portion to be passed.
Figure 30:
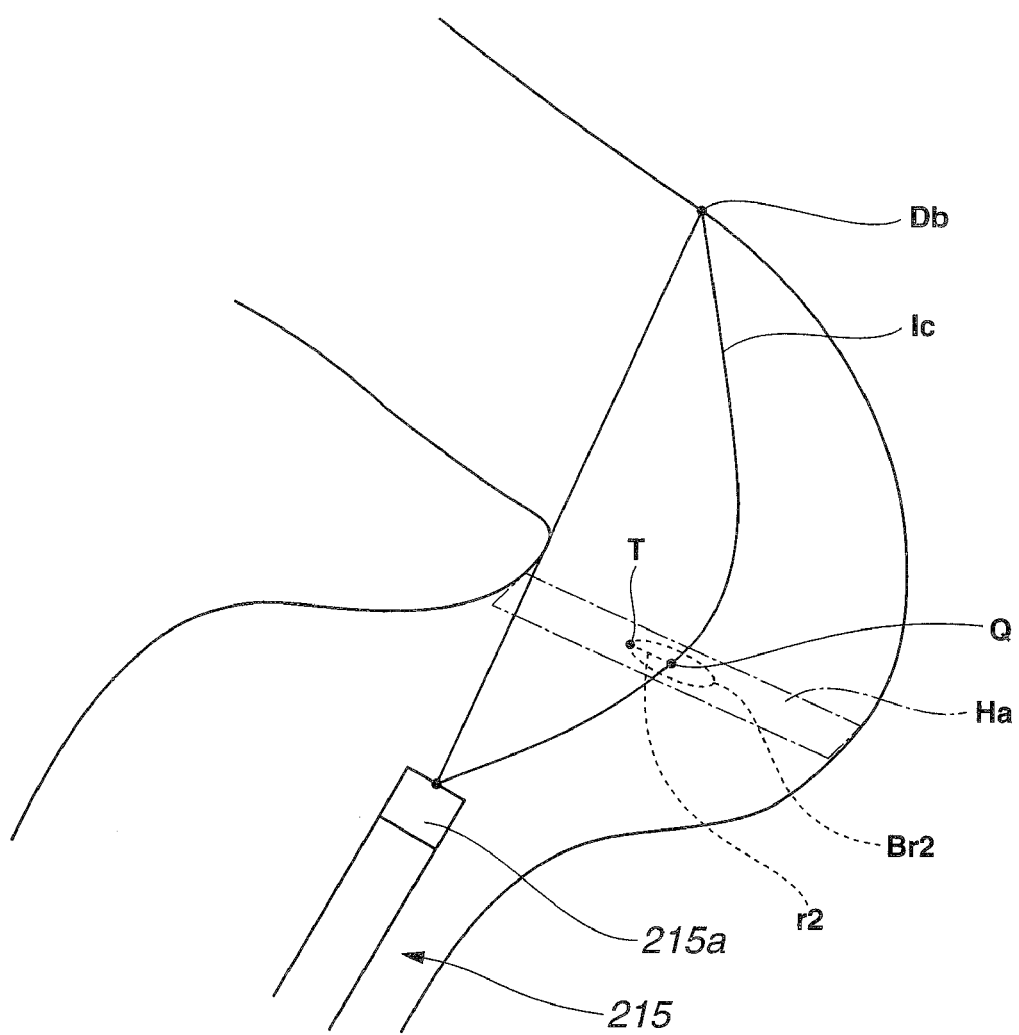
FIG. 30 is a view showing an example of processing of calculating a target position for the distal end portion to be passed, which is different from the example in FIG. 29.

FIGS. 24 to 32 relate to an embodiment of the present invention. FIG. 24 is a view showing a configurational example of a main part of an endoscope system according to the third embodiment of the present invention. FIG. 25 is a flowchart showing an example of processing for setting a path for the distal end portion to be passed. FIG. 26 is a flowchart showing an example of processing performed for setting a content of the bending control performed with respect to the bending portion. FIG. 27 is a view showing an example of a shape of a lumen in the vicinity of the current position of the distal end portion. FIG. 28 is a schematic diagram related to a brief overview of the processing shown in the flowchart in FIG. 25. FIG. 29 is a view showing an example of processing of calculating a target position for the distal end portion to be passed. FIG. 30 is a view showing an example of processing of calculating a target position for the distal end portion to be passed, which is different from the example shown in FIG. 29. FIG. 31 is a view showing an example of processing which can be added to the processing in the flowchart in FIG. 26. FIG. 32 is a schematic diagram related to a brief overview of the processing in the flowchart in FIG. 31.

As shown in FIG. 24, an endoscope system 201 according to the third embodiment of the present invention includes: an endoscope 202 which is to be inserted into a body cavity of a patient as a subject and which picks up an image of a photographic subject in the body cavity; a processor 206 to and from which a connector 214 provided in the endoscope 202 is attachable and detachable; a sense coil unit 207 arranged around a bed on which the patient lies; an endoscope insertion shape detecting apparatus 208; a terminal apparatus 209; a monitor 210a, and a monitor 210b.

In addition, the processor 206 includes: a light source section 203 that supplies illumination light for illuminating a photographic subject as an image pickup object to the endoscope 202; a signal processing section 204 that generates a video signal by performing signal processing on an image pickup signal outputted from the endoscope 202 and outputs the generated video signal; a bending control section 205 that performs bending control on the endoscope 202; and a source coil driving section 243.

The endoscope 202 includes an elongated insertion portion 211 to be inserted in the body cavity (lumen) of a subject; an operation portion 212 provided at a rear end of the insertion portion 211; and a universal cord 213 extended from the operation portion 212. The connector 214 that is attachable and detachable to and from the processor 206 is provided at a rear end of the universal cord 213.

The insertion portion 211 includes: a rigid distal end portion 215 provided on a distal end side; a bending portion 216 connected to a rear end of the distal end portion 215; and a flexible tube portion 217 having flexibility that is provided between a rear end of the bending portion 216 and a front end of the operation portion 212. Furthermore, q-pieces of source coils $C_1$, $C_2$, . . . , and $C_q$ that generate magnetic fields corresponding to the source coil driving signals applied by the source coil driving section 243 are provided in the insertion portion 211 at substantially equal intervals.

The distal end portion 215 is provided with an image pickup section 215a including an objective optical system that forms an image of a photographic subject and an image pickup device that outputs the image of the photographic subject formed through the objective optical system as an image pickup signal.

The operation portion 212 is provided with a scope switch 218 that gives an instruction for acquiring a freeze image (still image), for example; a bending mode switching switch 219 that gives an instruction for switching the bending mode of the bending portion 216 to either the manual bending mode or the automatic bending mode; a joystick 220 for bending operation that gives instructions on the bending direction and the bending angle of the bending portion 216 when the manual bending mode is selected. In addition, at a portion on a rear end side of the flexible tube portion 217 and near the front end of the operation portion 212 is provided a treatment instrument insertion port 239 leading to a channel for treatment instrument, not shown, through which a treatment instrument and the like is insertable.

A light guide 221 that transmits the illumination light supplied from the light source section 203 to the distal end portion 215 is inserted in the insertion portion 211 and the like of the endoscope 202.

One end surface (incident end surface) of the light guide 221 is arranged protruding from the connector 214. Furthermore, the other end surface (light-emitting end surface) of the light guide 221 is arranged in the vicinity of an illumination optical system, not shown, provided in the distal end portion 215. According to such a configuration, in a state where the connector 214 is connected to the processor 206, the illumination light supplied from the light source section 203 passes through the light guide 221 and the illumination optical system, not shown, and thereafter illuminates the photographic subject as the image pickup object of the image pickup section 215a.

The light source section 203, for example, includes: a lamp 222 that emits illumination light which is white light; a lamp driving section 223 that supplies a power source required for driving the lamp 222; a diaphragm 224; a diaphragm control section 225 that increases and decreases the diaphragm amount (opening amount) of the diaphragm 224 based on the video signal outputted from the signal processing section 204; and a light condensing optical system 226 that condenses the illumination light passed through the diaphragm 224 and supplies the illumination light to the incident end surface of the light guide 221.

The diaphragm control section 225, for example, calculates the average brightness based on the luminance components of the inputted video signal, and appropriately changes the light amount of the illumination light passing through the diaphragm 224 by increasing and decreasing the diaphragm amount (opening amount) of the diaphragm 224 based on a difference value which is a value obtained by subtracting a reference value corresponding to the appropriate brightness from the average brightness.

The signal processing section 204 includes: an image pickup device driving section 236 that outputs an image pickup device driving signal for driving the image pickup device provided in the image pickup section 215a; and a video processing section 237 that generates a video signal by performing signal processing on the image pickup signal outputted from the image pickup section 215a and outputs the generated video signal. According to this configuration, an endoscopic image 1a2 according to the video signal is displayed on the monitor 210a.

When the bending mode of the bending portion 216 is switched to the manual bending mode based on the instruction given by the bending mode switching switch 219, the bending control section 205 performs control to change the bending direction and the bending angle of the bending portion 216 based on the inclination direction and inclination amount of the joystick 220 for bending operation. In addition, when the bending mode of the bending portion 216 is switched to the automatic bending mode based on the instruction given by the bending mode switching switch 219, the bending control section 205 performs control to change the bending direction and the bending angle of the bending portion 216 based on the arithmetic operation result from the terminal apparatus 209.

The source coil driving section 243 is connected to the q-pieces of source coils $C_1, C_2, \ldots, C_q$ provided in the insertion portion 211, and sequentially applies an alternate current source coil driving signal to each of the source coils. As a result, an alternate current magnetic field is generated around each of the source coils provided in the insertion portion 211.

The sense coil unit 207 is provided with a sense coil group 244 that detects the magnetic field generated from each of the q-pieces of source coils $C_1, C_2, C_q$ provided in the insertion portion 211 and outputs the magnetic fields as magnetic field detection signals.

The endoscope insertion shape detecting apparatus 208 includes: an amplifier 245 that amplifies the magnetic field detection signals outputted from the sense coil unit 207; a source coil position/orientation detecting section 246 that detects three-dimensional coordinate positions and orientations of the q-pieces of source coils $C_1, C_2, \ldots,$ and $C_q$ based on the magnetic field detection signals outputted from the amplifier 245, and outputs the detected three-dimensional coordinate positions and orientations as three-dimensional coordinate information; and an insertion shape estimating section 247 that estimates the insertion shape of the insertion portion 211 based on the insertion shape information outputted from the source coil position/orientation detecting section 246, and outputs the estimated insertion shape as an insertion shape image signal. According to this configuration, an insertion shape image 1b2 of the insertion portion 211 according to the insertion shape image signal is displayed on the monitor 210b.

The terminal apparatus 209 includes an arithmetic processing section 291 that performs arithmetic operation related to the bending control performed in the case where the bending mode of the bending portion 216 is the automatic mode, based on the video signal outputted from the video processing section 237 and the insertion shape information outputted from the source coil position/orientation detecting section 246, and outputs the arithmetic operation result to the bending control section 205. Note that the specific content of the arithmetic operation performed in the arithmetic processing section 291 will be described later.

Next, the working of the endoscope system 201 will be described. Note that description on the control in the case where the bending mode switching switch 219 is switched to the manual bending mode will be omitted below, and description will be mainly made on the control in the case where the bending mode switching switch 219 is switched to the automatic bending mode.

First, an operator connects and activates each part of the endoscope system 201, and thereafter inserts the insertion portion 211 of the endoscope 202 into the body cavity of a patient and switches the bending mode switching switch 219 to the automatic bending mode. In response to this, the image pickup section 215a in the endoscope 202 starts picking up an image of a photographic subject, and each of the source coils provided in the insertion portion 211 starts to generate a magnetic field.

The image pickup signal outputted from the image pickup section 215a in association with the image pickup of the photographic subject is outputted to the processor 206 through the universal cord 213 and the connector 214, to be converted into a video signal in the video processing section 237, and thereafter inputted to the arithmetic processing section 291 in the terminal apparatus 209. In addition, the magnetic field detection signals outputted from the sense coil unit 207 in association with the generation of magnetic fields from the source coils provided in the insertion portion 211 are amplified in the amplifier 245 to be converted as the three-dimensional coordinate information of the source coils by the source coil position/orientation detecting section 246, and thereafter inputted to the arithmetic processing section 291 in the terminal apparatus 209.

The arithmetic processing section 291 in the terminal apparatus 209 performs processing based on the inputted video signal and the three-dimensional coordinate information of the source coils, thereby setting the path for the distal end portion 215 to be passed and setting the control content for bending the bending portion 216 such that the distal end portion 215 is advanced substantially along the path.

Now, description will be made on the processing performed by the arithmetic processing section 291 in order to set the path for the distal end portion 215 to be passed, with reference to FIG. 25 and the like.

The arithmetic processing section 291 acquires image data based on the video signal inputted thereto (step S201 in FIG. 25), and thereafter performs distortion correction on the image data. By performing the processing steps described above, the arithmetic processing section 291 acquires two-dimensional image data in which a monochrome portion is eliminated from the original image based on the inputted video signal.

Next, the arithmetic processing section 291 having a function as a three-dimensional shape calculating section calculates, based on the two-dimensional image data acquired by the processing in the step S201 in FIG. 25, three-dimensional shape data as data showing the shape of the lumen in the vicinity of the current position of the distal end portion 215 by using the Shape From Shading method, for example (step S202 in FIG. 25). According to this processing, the arithmetic processing section 291 detects that the shape of the lumen in the vicinity of the current position of the distal end portion 215 has a flexed portion formed by the folds and the like in the body cavity, as shown in FIG. 27, for example.

Then, the arithmetic processing section 291 sets a local coordinate system with the origin thereof at a predetermined position on the distal end surface of the distal end portion 215, the x-axis on an axis corresponding to the left/right direction of the image data acquired by the processing in the step S201 in FIG. 25, the y-axis on an axis corresponding to up/down direction of the image data, and the z-axis on an axis corresponding to the depth direction of the image data, for example, with respect to the three-dimensional shape data calculated by the processing in the step S202 in FIG. 25 (step S203 in FIG. 25).

After that, the arithmetic processing section 291 having a function as a cutting surface acquiring section acquires, based on the image data acquired by the processing in the step S201 in FIG. 25 and the three-dimensional shape data calculated by the processing in the step S202 in FIG. 25, K-pieces of cutting surface data within the field of view range of the endoscope 202 (or in the vicinity of the position where the distal end portion 215 exists) (step S204 in FIG. 25).

In the processing in the step S204 in FIG. 25, first the arithmetic processing section 291 detects the position of the dark point (the darkest point) in the three-dimensional shape data, based on the image data acquired by the processing in the step S201 in FIG. 25 and the three-dimensional shape data calculated by the processing in the step Sin FIG. 25. Specifically, the arithmetic processing section 291 detects the point Db shown in FIG. 28 as the dark point (the darkest point).

In the processing in the step S204 in FIG. 25, next the arithmetic processing section 291 acquires K-pieces of cutting surface data by cutting the three-dimensional shape data using K-pieces of planes which are perpendicular to the vector pointing from a predetermined position of the distal end surface of the distal end portion 215 to the point Db and which are set at substantially equal intervals. Specifically, the arithmetic processing section 291 acquires four pieces of data of the planes H1, H2, H3 and H4 shown in FIG. 28, as cutting surface data, for example.

The arithmetic processing section 291 sets a variable i ($1 \leq i \leq K$) corresponding to the number attached to each piece of the cutting surface data acquired by the processing in step S204 in FIGS. 25 to 1 (step S205 in FIG. 25), and thereafter extracts the edge of the i-th cutting surface data (step S206 in FIG. 25). Specifically, the arithmetic processing section 291 reduces the cutting surface data, and thereafter extracts the edge of the cutting surface data by applying any one of the Canny, Sobel or Laplacian algorithms to the reduced cutting surface data.

The arithmetic processing section 291 determines whether or not the edge of the cutting surface data extracted by the processing in the step S206 in FIG. 25 is closed curve (step S207 in FIG. 25). When detecting that the edge of the cutting surface data extracted by the processing in the step S206 in FIG. 25 is closed curve, the arithmetic processing section 291 calculates the centroid of the cutting surface data (step S208 in FIG. 25). In addition, when detecting that the edge of the cutting surface data extracted by the processing in the step S206 in FIG. 25 is not closed curve, the arithmetic processing section 291 forms a hypothetical circle including at least a part of the edge on the outer circumference thereof using the circle Hough transform and then calculates the center point of the hypothetical circle (step S209 in FIG. 25).

That is, the arithmetic processing section 291 performs the processing of extracting the cross-sectional shape of the cutting surface of the three-dimensional data of the lumen and detecting a path point corresponding to the cross-sectional shape of each of the cutting surfaces, as the processing in the steps S206 to S209 in FIG. 25.

The arithmetic processing section 291 repeatedly performs the processing shown in the steps S206 to S209 in FIG. 25 until the variable i becomes equal to K (step S210 in FIG. 25). Among the K-pieces of cutting surface data, as for the cutting surface data subjected to the processing in the step S208 in FIG. 25, the centroid is calculated, and as for the cutting surface data subjected to the processing in the step S209, the center point of the hypothetical circle is calculated. Specifically, the arithmetic processing section 291 repeatedly performs the processing in the steps S206 to S209 in FIG. 25, thereby calculating the points E1, E2, E3, and E4 on the plane H1, H2, H3, and H4, respectively, as shown in FIG. 28, for example.

When the calculation of the centroid or the center point of the hypothetical circle in each of the K-pieces of cutting surface data is completed, the arithmetic processing section 291 having a function as a path calculating section calculates a path line as a segment which passes K-pieces of points including the centroid and the center point of the hypothetical circle, a predetermined position on a distal end surface of the distal end portion 215, and the point Db (step S211 in FIG. 25), and thereafter repeatedly performs a series of processing steps from the step S201 in FIG. 25. Note that the arithmetic processing section 291 calculates, as the path line, a parametric curve calculated by applying Catmull Rom curve equation to each of the points, for example. Specifically, by performing the processing in the step S211 in FIG. 25, the arithmetic processing section 291 calculates, as the path line, a curve Ic passing the points E1, E2, E3 and E4 as the path points, the predetermined position on the distal end surface of the distal end portion 215, and the point Db, as shown in FIG. 28, for example.

Furthermore, the arithmetic processing section 291 performs the processing shown in the flowchart in FIG. 26 in parallel with the processing shown in the flowchart in FIG. 25.

The arithmetic processing section 291 calculates the current position and orientation of the distal end portion 215 based on the three-dimensional coordinate information outputted from the source coil position/orientation detecting section 246 (step S221 in FIG. 26).

After that, the arithmetic processing section 291 determines whether or not the distal end portion 215 has passed through the target position, to be set by the processing described below, for the distal end portion 215 to be passed (step S222 in FIG. 26). When determining that the distal end portion 215 has passed through the target position, the arithmetic processing section 291 calculates a new path line with the predetermined position on the distal end surface of the distal end portion 215 as a starting point by the processing shown in the flowchart in FIG. 25 (step S223 in FIG. 26). When determining that the distal end portion 215 has not passed through the target position, the arithmetic processing section 291 subsequently performs the processing in step S224 in FIG. 26 while retaining the target position and the path line related to the target position.

That is, the arithmetic processing section 291 having the function as the path calculating section performs the processing for calculating a new path line with the predetermined position on the distal end surface of the distal end portion 215 as a starting point, every time the distal end portion 215 passes through the target position set by the processing to be described later.

Based on the three-dimensional coordinate information outputted from the source coil position/orientation detecting section 246, the arithmetic processing section 291 calculates a moving velocity of the source coil $C_1$ per unit time, for example, thereby calculating the moving distance r1 of the distal end portion 215 after Δt seconds (step S224 in FIG. 26).

The arithmetic processing section 291 calculates the target position for the distal end portion 215 to be passed based on the path line Ic and the moving distance r1 (step S225 in FIG. 26).

In the processing in the step S225 in FIG. 26, the arithmetic processing section 291 sets a hypothetical globe Br1 with the predetermined position on the distal end surface of the distal end portion 215 as a center point and the moving distance r1 as a radius, as shown in FIG. 29, and thereafter calculates the three-dimensional coordinate position of a point Q where the hypothetical globe Br1 and the curve Ic intersect with each other. Then, the arithmetic processing section 291 calculates the three-dimensional coordinate position of the point Q as the target position for the distal end portion 215 to be passed.

The arithmetic processing section 291 of the present embodiment calculates the three-dimensional coordinate position of the point Q by the processing in step S225 in FIG. 26, and thereafter may correct the target position by further performing the processing steps described below.

Specifically, the arithmetic processing section 291 calculates the three-dimensional coordinate position of the point Q, and thereafter calculates a plane Ha including the point Q and perpendicular to the vector pointing from the predetermined position on the distal end surface of the distal end portion 215 to the point Db, as shown in FIG. 30, for example.

The arithmetic processing section 291 forms a hypothetical circle Br2 which includes the point Q as the center point and exists on the plane Ha with the radius r2, and thereafter calculates the three-dimensional coordinate position of a point T among the points on the circle Br2, which exists on the same plane as the path line Ic, as a corrected target position.

That is, the arithmetic processing section 291 having a function as a target position correction section performs the processing steps described above, thereby capable of calculating the three-dimensional coordinate position of the point T as the corrected target position at which the amount of bending of the bending portion 216 can be reduced compared with the case where the point Q is set as the target position.

Meanwhile, the arithmetic processing section 291 calculates the amount of bending and the bending direction of the bending portion 216 such that the distal end portion 215 moves toward the target position set in the step S225 in FIG. 26 (step S226 in FIG. 26).

Based on the amount of bending and the bending direction of the bending portion 216 calculated by the processing in the step S226 in FIG. 26, the arithmetic processing section 291 performs arithmetic operation of the bending control information which is necessary for actually bending the bending portion 216 (step S227 in FIG. 26), and outputs the arithmetic operation result to the bending control section 205. After that, the arithmetic processing section 291 repeatedly performs a series of processing steps from the step S221 in FIG. 26 again.

Note that, when the bending portion 216 includes a plurality of bending pieces and the like connected to one end side of the wire and is configured to be capable of changing the bending state thereof according to the tension or relaxation of the wire caused by the rotational driving of the motor, for example, the above-described bending control information is assumed to be shown as the information related to the angles of the pulleys connected to the motor and the driving voltages applied to the motors. In addition, when the bending portion 216 has an alternative configuration other than the above-described configuration, for example, the above-described bending control information is assumed to be shown as information corresponding to the alternative configuration.

As described above, the endoscope system 201 of the present embodiment is configured to perform the processing shown in FIG. 25 and FIG. 26 in the automatic bending mode, thereby capable of controlling the bending portion of the endoscope such that the endoscope distal end portion is advanced toward (the lumen on) the rear side of the folds forming a flexed portion in the lumen as shown in FIG. 27, for example, while preventing the endoscope distal end portion from contacting the folds. According to such a configuration, the endoscope system 201 of the present embodiment can improve the insertion performance of the endoscope compared with conventional systems.

Note that the arithmetic processing section 291 of the present embodiment may further perform the processing steps shown in the flowchart in FIG. 31, between the step S223 and the step S224 in FIG. 26.

First, the arithmetic processing section 291 calculates a radius of curvature F of the path line calculated in the step S223 in FIG. 26 (step S231 in FIG. 31).

Next, the arithmetic processing section 291 determines whether or not the radius of curvature F calculated by the processing in step S231 in FIG. 31 is larger than a threshold THF (step S232 in FIG. 31). When determining that the radius of curvature F is larger than the threshold THF, the arithmetic processing section 291 performs the processing in step S233 in FIG. 31 to be described later. Furthermore, when determining that the radius of curvature F is equal to or smaller than the threshold THF, the arithmetic processing section 291 uses the path line calculated in step S211 in FIG. 25 as the processing result, and subsequently performs the processing in step S224 in FIG. 26.

When determining that the radius of curvature F is larger than the threshold THF, the arithmetic processing section 291 calculates the plane Hb including the entire path line calculated in the step S211 in FIG. 25 (step S233 in FIG. 31).

After that, the arithmetic processing section 291 projects the three-dimensional shape data calculated in the step S202 in FIG. 25 and the path line calculated in the step S211 in FIG. 25 on the coordinate system of the plane Hb (step S234 in FIG. 31).

Note that the coordinate system of the plane Hb is defined with the axis with the largest variance of the path line calculated in the step S211 in FIG. 25 as a first principal component axis and the peak direction of the path line as a second principal component axis, as shown in FIG. 32, for example. The three-dimensional shape data and the path line representing the shape of the lumen are respectively projected on the coordinate system of the plane Hb as the states shown in FIG. 32, for example, by the processing in step S234 in FIG. 31.

The arithmetic processing section 291 performs transform processing for reducing nearly generally the second principal component of the path line which is projected on the coordinate system in the plane Hb (step S235 in FIG. 31). According to the processing, the arithmetic processing section 291 acquires the path line as shown in FIG. 32, for example, as the path line subjected to the transform processing.

The arithmetic processing section 291 then acquires a new path line by reversely projecting the path line subjected to the transform processing on the coordinate system of the three-dimensional shape data as the coordinate system set by the processing in step S203 in FIG. 25, for example, (step S236 in FIG. 31), and thereafter subsequently performs the above-described processing in the step S224 in FIG. 26.

By further performing the above-described processing steps between the step S223 and the step S224 in FIG. 26, the arithmetic processing section 291 of the present embodiment can calculate the path line for advancing the distal end portion 215 such that the distal end portion passes through the vicinity of the wall surface on the inner circumferential side of the extremely flexed region in the lumen.

Note that, if the determination condition in the step S232 in FIG. 31 and the content of the transform processing in the step S235 are appropriately changed, the processing shown in the flowchart in FIG. 31 can be also applied to the case where the path line is calculated for advancing the distal end portion 215 along the surface (stomach wall) of the lumen having a large diameter such as a stomach, for example.

That is, in the present embodiment, the arithmetic processing section 291 further performs the processing shown in the flowchart in FIG. 31, thereby enabling detailed observation of the state of the surface of the lumen while preventing the distal end portion 215 from contacting the surface of the lumen.

Note that embodiments and the like configured by partially combining the above-described embodiments and the like also belong to the present invention.

Having described the preferred embodiments of the invention referring to the accompanying drawings, it should be understood that the present invention is not limited to those precise embodiments and various changes and modifications thereof could be made by one skilled in the art without departing from the sprit or scope of the invention as defined in the appended claims.

What is claimed is:

1. An endoscope bending control apparatus comprising:
    an image feature value calculating section for calculating, based on an endoscopic image acquired by an image pickup device in an endoscope including the image pickup device and a bending portion on a distal end side of an insertion portion, an image feature value related to a luminal dark part in a lumen into which the insertion portion is inserted;
    a bending control section for performing bending control on the bending portion in either one of a first bending operation mode in which a position of the luminal dark part is set as an insertion target based on the calculated image feature value and a distal end of the insertion portion is directed to the position and a second bending operation mode in which a current position of the luminal dark part is estimated with reference to history information including the position of the luminal dark part calculated in the past and the distal end of the insertion portion is directed in a direction of the estimated position of the luminal dark part;
    an operation mode switching section for switching an operation mode from one of the first and the second bending operation modes to the other of the first and the second bending operation modes according to a first switching condition based on the calculated image feature value; and
    a switching condition changing section for changing a switching condition from the first switching condition used for switching between the bending operation modes to a second switching condition different from the first switching condition.

2. The endoscope bending control apparatus according to claim 1, further comprising
    a storage section for storing the history information, wherein the storage section stores information on the position of the luminal dark part and information on a position and a direction of the distal end of the insertion portion as the history information.

3. The endoscope bending control apparatus according to claim 2, wherein the storage section stores the information on the position of the luminal dark part and the information on the position and the direction of the distal end of the insertion portion as the history information in an order of time elapse.

4. The endoscope bending control apparatus according to claim 1, wherein the switching condition changing section changes a feature value parameter included in the first switching condition or the second switching condition, based on a detection result from an insertion shape detecting section for detecting an insertion shape including a position of a distal end side of the insertion portion.

5. The endoscope bending control apparatus according to claim 1, wherein the first switching condition or the second switching condition is changed and set according to a location along an insertion path in the lumen into which the insertion portion is inserted.

6. The endoscope bending control apparatus according to claim 1, wherein the first switching condition and the second switching condition are set in advance according to an insertion length by which the insertion portion is inserted into the lumen.

7. The endoscope bending control apparatus according to claim 1, wherein the switching condition changing section changes the switching condition from the first switching condition to the second switching condition using information on an insertion length by which the insertion portion is inserted into the lumen.

8. The endoscope bending control apparatus according to claim 1, wherein when the switching condition is changed to the second switching condition, the switching condition changing section further changes the second switching condition to a third switching condition different from the second switching condition according to an insertion length by which the insertion portion is inserted into the lumen.

9. The endoscope bending control apparatus according to claim 1, further comprising an insertion shape detecting section for detecting an insertion shape including a position of a distal end side of the insertion portion.

10. The endoscope bending control apparatus according to claim 1, wherein the first switching condition and the second switching condition are set by respectively using a different plurality of feature value parameters.

11. The endoscope bending control apparatus according to claim 10, wherein the first switching condition and the second switching condition are set by using the plurality of feature value parameters according to a location in an insertion path along which the insertion portion is inserted into the lumen.

12. The endoscope bending control apparatus according to claim 1, wherein the first switching condition and the second switching condition are used in a form of path list in which feature value parameters included in the first switching condition and the second switching condition are listed according to a first path location and a second path location as locations along an insertion path in the lumen into which the insertion portion is inserted.

13. The endoscope bending control apparatus according to claim 12, wherein the path list is selected and used according to a kind of a luminal organ into which the insertion portion is inserted.

14. The endoscope bending control apparatus according to claim 1, wherein the image feature value calculating section calculates at least one feature value among a distance from the distal end of the insertion portion to the luminal dark part, a ratio of including a halation pixel whose pixel level is saturated, and a ratio of including a dark-part pixel whose pixel level is close to a black level, from data of the endoscopic image, as the image feature value.

15. The endoscope bending control apparatus according to claim 1, further comprising a rotation angle detecting section for detecting a rotation angle around an insertion axis of the insertion portion.

16. The endoscope system according to claim 1, wherein the first switching condition and the second switching condition are set by respectively using a different plurality of feature value parameters.

17. An endoscope system comprising:
an endoscope including, at a distal end side of an insertion portion thereof, an image pickup device and a bending portion;
a signal processing apparatus to which the endoscope is connected, the signal processing apparatus generating an endoscopic image based on an output signal from the image pickup device;
an image feature value calculating section for calculating, based on the endoscopic image, an image feature value related to a luminal dark part in a lumen into which the insertion portion is inserted;
a bending control section for performing bending control on the bending portion in either one of a first bending operation mode in which a position of the luminal dark part is set as an insertion target based on the calculated image feature value and a distal end of the insertion portion is directed to the position and a second bending operation mode in which a current position of the luminal dark part is estimated with reference to history information including the position of the luminal dark part calculated in the past and the distal end of the insertion portion is directed in a direction of the estimated position of the luminal dark part;
an operation mode switching section for switching an operation mode from one of the first and the second bending operation modes to other of the first and the second bending operation modes according to a first switching condition based on the calculated image feature value; and
a switching condition changing section for changing a switching condition from the first switching condition used for switching between the bending operation modes to a second switching condition different from the first switching condition.

18. The endoscope system according to claim 17, further comprising a storage section for storing the history information, wherein the storage section stores the position of the luminal dark part and information on a position and a direction of the distal end of the insertion portion as the history information.

19. The endoscope system according to claim 17, wherein the switching condition changing section changes a feature value parameter included in the first switching condition or the second switching condition, based on a detection result from an insertion shape detecting section for detecting an insertion shape including a position of a distal end side of the insertion portion.

20. The endoscope system according to claim 16, wherein the first switching condition and the second switching condition are set in advance according to an insertion length by which the insertion portion is inserted into the lumen.

* * * * *

UNITED STATES PATENT AND TRADEMARK OFFICE
CERTIFICATE OF CORRECTION

PATENT NO. : 8,211,009 B2
APPLICATION NO. : 12/764482
DATED : July 3, 2012
INVENTOR(S) : Hideki Tanaka et al.

It is certified that error appears in the above-identified patent and that said Letters Patent is hereby corrected as shown below:

In the Claims:

Column 36, line 64 (claim 16, line 1) should read: The endoscope system according to claim 17, wherein Column 38, line 22 (claim 20, line 1) should read: The endoscope system according to claim 17, wherein Signed and Sealed this
Twenty-third Day of April, 2013

Teresa Stanek Rea
*Acting Director of the United States Patent and Trademark Office*